(12) United States Patent
Jones

(10) Patent No.: US 12,350,187 B2
(45) Date of Patent: Jul. 8, 2025

(54) FLUID COLLECTION ASSEMBLIES DEFINING WAIST AND LEG OPENINGS

(71) Applicant: PureWick Corporation, El Cajon, CA (US)

(72) Inventor: Jill W. Jones, Atlanta, GA (US)

(73) Assignee: PureWick Corporation, Covington, GA (US)

( * ) Notice: Subject to any disclaimer, the term of this patent is extended or adjusted under 35 U.S.C. 154(b) by 0 days.

(21) Appl. No.: 17/444,792

(22) Filed: Aug. 10, 2021

(65) Prior Publication Data

US 2022/0054298 A1    Feb. 24, 2022

Related U.S. Application Data

(60) Provisional application No. 63/064,126, filed on Aug. 11, 2020.

(51) Int. Cl.
| | | |
|---|---|---|
| *A61F 5/44* | (2006.01) | |
| *A61F 5/451* | (2006.01) | |
| *A61M 1/00* | (2006.01) | |

(52) U.S. Cl.
CPC ............ *A61F 5/4404* (2013.01); *A61F 5/451* (2013.01); *A61M 1/73* (2021.05); *A61M 1/74* (2021.05)

(58) Field of Classification Search
CPC .......... A61F 5/451; A61F 5/44; A61F 5/4404; A61F 5/455; A61F 5/48; A61F 5/4405; A61F 5/4407; A61F 5/453; A61F 13/05; A61G 9/006; A61G 9/00
See application file for complete search history.

(56) References Cited

U.S. PATENT DOCUMENTS

| | | | |
|---|---|---|---|
| 670,602 | A | 3/1901 | Baker |
| 737,443 | A | 8/1903 | Mooers |
| 1,015,905 | A | 1/1912 | Northrop |
| 1,032,841 | A | 7/1912 | Koenig |
| 1,178,644 | A | 4/1916 | Johnson |
| 1,387,726 | A | 8/1921 | Karge |

(Continued)

FOREIGN PATENT DOCUMENTS

| | | |
|---|---|---|
| AU | 2018216821 A1 | 8/2019 |
| AU | 2021299304 A1 | 2/2023 |

(Continued)

OTHER PUBLICATIONS

US 9,908,683 B2, 03/2018, Sandhausen et al. (withdrawn)

(Continued)

*Primary Examiner* — Adam Marcetich
*Assistant Examiner* — Ted Yang
(74) *Attorney, Agent, or Firm* — Dorsey & Whitney LLP

(57) ABSTRACT

An example fluid collection assembly includes a fluid impermeable barrier. The fluid impermeable barrier at least partially defines a waist opening and two leg openings. The waist opening and the two leg openings are configured to have a waist and two legs of an individual positioned therein, respectively. The fluid impermeable barrier also defines at least one fluid outlet. The fluid collection assembly further includes at least one porous material conforming to at least a portion of the fluid impermeable barrier. The porous material may be adjacent to the outlet defined by the fluid impermeable barrier.

22 Claims, 8 Drawing Sheets

(56) References Cited

U.S. PATENT DOCUMENTS

| | | | |
|---|---|---|---|
| 1,742,080 | A | 12/1929 | Jones |
| 1,979,899 | A | 11/1934 | Obrien et al. |
| 2,241,010 | A | 5/1941 | Chipley |
| 2,262,772 | A | 11/1941 | Peder |
| 2,326,881 | A | 8/1943 | Packer |
| 2,379,346 | A | 6/1945 | Farrell |
| 2,485,555 | A | 10/1949 | Bester |
| 2,571,357 | A | 10/1951 | Charles |
| 2,613,670 | A | 10/1952 | Edward |
| 2,616,426 | A | 11/1952 | Adele |
| 2,644,234 | A | 7/1953 | Earl |
| 2,648,335 | A | 8/1953 | Chambers |
| 2,859,786 | A | 11/1958 | Tupper |
| 2,944,551 | A * | 7/1960 | Breer ............ A61F 5/455 4/144.1 |
| 2,968,046 | A | 1/1961 | Duke |
| 2,971,512 | A | 2/1961 | Reinhardt |
| 3,032,038 | A | 5/1962 | Swinn |
| 3,077,883 | A | 2/1963 | Hill |
| 3,087,938 | A | 4/1963 | Hans et al. |
| 3,169,528 | A | 2/1965 | Knox et al. |
| 3,171,506 | A | 3/1965 | Therkel |
| 3,194,238 | A * | 7/1965 | Breece, Jr. ............ A61F 5/455 D24/112 |
| 3,198,994 | A | 8/1965 | Hildebrandt et al. |
| 3,221,742 | A | 12/1965 | Egon |
| 3,312,221 | A | 4/1967 | Overment |
| 3,312,981 | A | 4/1967 | Mcguire et al. |
| 3,349,768 | A | 10/1967 | Keane |
| 3,362,590 | A | 1/1968 | Gene |
| 3,366,116 | A | 1/1968 | Huck |
| 3,398,848 | A | 8/1968 | Donovan |
| 3,400,717 | A | 9/1968 | Bruce et al. |
| 3,406,688 | A | 10/1968 | Bruce |
| 3,424,163 | A | 1/1969 | Gravdahl |
| 3,425,471 | A | 2/1969 | Yates |
| 3,511,241 | A | 5/1970 | Lee |
| 3,512,185 | A | 5/1970 | Ellis |
| 3,520,300 | A | 7/1970 | Flower |
| 3,528,423 | A | 9/1970 | Lee |
| 3,613,123 | A | 10/1971 | Langstrom |
| 3,648,700 | A | 3/1972 | Warner |
| 3,651,810 | A | 3/1972 | Ormerod |
| 3,661,155 | A | 5/1972 | Lindan |
| 3,683,918 | A | 8/1972 | Pizzella |
| 3,699,815 | A | 10/1972 | Holbrook |
| 3,726,277 | A | 4/1973 | Hirschman |
| 3,742,952 | A | 7/1973 | Magers et al. |
| 3,757,355 | A | 9/1973 | Allen et al. |
| 3,788,324 | A | 1/1974 | Lim |
| 3,843,016 | A | 10/1974 | Bornhorst et al. |
| 3,863,638 | A | 2/1975 | Rogers et al. |
| 3,863,798 | A | 2/1975 | Kurihara et al. |
| 3,864,759 | A | 2/1975 | Horiuchi |
| 3,865,109 | A | 2/1975 | Elmore et al. |
| 3,881,486 | A | 5/1975 | Fenton |
| 3,881,489 | A | 5/1975 | Hartwell |
| 3,915,189 | A | 10/1975 | Holbrook et al. |
| 3,998,228 | A | 12/1976 | Poidomani |
| 3,999,550 | A | 12/1976 | Martin |
| 4,015,604 | A | 4/1977 | Csillag |
| 4,020,843 | A | 5/1977 | Kanall |
| 4,022,213 | A | 5/1977 | Stein |
| 4,027,776 | A | 6/1977 | Douglas |
| 4,064,962 | A | 12/1977 | Hunt |
| 4,116,197 | A * | 9/1978 | Bermingham ........ A61F 5/455 604/347 |
| 4,180,178 | A | 12/1979 | Turner |
| 4,187,953 | A | 2/1980 | Turner |
| 4,194,508 | A | 3/1980 | Anderson |
| 4,200,102 | A | 4/1980 | Duhamel et al. |
| 4,202,058 | A | 5/1980 | Anderson |
| 4,203,503 | A | 5/1980 | Bertotti et al. |
| 4,209,076 | A | 6/1980 | Bertotti et al. |
| 4,223,677 | A | 9/1980 | Anderson |
| 4,233,025 | A | 11/1980 | Larson et al. |
| 4,246,901 | A | 1/1981 | Frosch et al. |
| 4,253,542 | A | 3/1981 | Ruspa et al. |
| 4,257,418 | A | 3/1981 | Hessner |
| 4,270,539 | A | 6/1981 | Frosch et al. |
| 4,281,655 | A * | 8/1981 | Terauchi ............ A61F 5/451 604/245 |
| 4,292,916 | A | 10/1981 | Bradley et al. |
| 4,330,239 | A | 5/1982 | Gannaway |
| 4,352,356 | A | 10/1982 | Tong |
| 4,360,933 | A | 11/1982 | Kimura et al. |
| 4,365,363 | A | 12/1982 | Windauer |
| 4,375,841 | A | 3/1983 | Vielbig |
| 4,387,726 | A | 6/1983 | Denard |
| 4,403,991 | A | 9/1983 | Hill |
| 4,425,130 | A | 1/1984 | Desmarais |
| 4,446,986 | A | 5/1984 | Bowen et al. |
| 4,453,938 | A | 6/1984 | Brendling |
| 4,457,314 | A | 7/1984 | Knowles |
| 4,476,879 | A | 10/1984 | Jackson |
| 4,526,688 | A | 7/1985 | Schmidt et al. |
| 4,528,703 | A | 7/1985 | Kraus |
| D280,438 | S | 9/1985 | Wendt |
| 4,551,141 | A | 11/1985 | McNeil |
| 4,553,968 | A | 11/1985 | Komis |
| 4,581,026 | A | 4/1986 | Schneider |
| 4,589,516 | A | 5/1986 | Inoue et al. |
| 4,601,716 | A | 7/1986 | Smith |
| 4,610,675 | A | 9/1986 | Triunfol |
| 4,620,333 | A | 11/1986 | Ritter |
| 4,626,250 | A | 12/1986 | Schneider |
| 4,627,846 | A | 12/1986 | Ternstroem |
| 4,631,061 | A | 12/1986 | Martin |
| 4,650,477 | A | 3/1987 | Johnson |
| 4,655,754 | A | 4/1987 | Richmond et al. |
| 4,656,675 | A | 4/1987 | Fajnsztajn |
| 4,681,570 | A | 7/1987 | Dalton |
| 4,681,577 | A | 7/1987 | Stern et al. |
| 4,692,160 | A | 9/1987 | Nussbaumer |
| 4,707,864 | A | 11/1987 | Ikematsu et al. |
| 4,713,065 | A | 12/1987 | Koot |
| 4,713,066 | A | 12/1987 | Komis |
| 4,723,953 | A | 2/1988 | Pratt et al. |
| 4,735,841 | A | 4/1988 | Sourdet |
| 4,743,236 | A | 5/1988 | Manschot |
| 4,747,166 | A | 5/1988 | Kuntz |
| 4,752,944 | A | 6/1988 | Conrads et al. |
| 4,769,215 | A | 9/1988 | Ehrenkranz |
| 4,771,484 | A | 9/1988 | Mozell |
| 4,772,280 | A | 9/1988 | Rooyakkers |
| 4,784,654 | A | 11/1988 | Beecher |
| 4,790,830 | A | 12/1988 | Hamacher |
| 4,790,835 | A | 12/1988 | Elias |
| 4,791,686 | A | 12/1988 | Taniguchi et al. |
| 4,795,449 | A | 1/1989 | Schneider et al. |
| 4,798,603 | A | 1/1989 | Meyer et al. |
| 4,799,928 | A | 1/1989 | Crowley |
| 4,804,377 | A | 2/1989 | Hanifl et al. |
| 4,812,053 | A | 3/1989 | Bhattacharjee |
| 4,813,943 | A | 3/1989 | Smith |
| 4,820,297 | A | 4/1989 | Kaufman et al. |
| 4,846,818 | A | 7/1989 | Keldahl et al. |
| 4,846,909 | A | 7/1989 | Klug et al. |
| 4,865,595 | A | 9/1989 | Heyden |
| 4,880,417 | A | 11/1989 | Yabrov et al. |
| 4,882,794 | A | 11/1989 | Stewart |
| 4,883,465 | A | 11/1989 | Brennan |
| 4,886,498 | A | 12/1989 | Newton |
| 4,886,508 | A | 12/1989 | Washington |
| 4,886,509 | A | 12/1989 | Mattsson |
| 4,889,532 | A | 12/1989 | Metz et al. |
| 4,889,533 | A | 12/1989 | Beecher |
| 4,890,691 | A | 1/1990 | Ching-ho |
| 4,903,254 | A | 2/1990 | Haas |
| 4,904,248 | A | 2/1990 | Vaillancourt |
| 4,905,692 | A | 3/1990 | More |
| 4,936,838 | A * | 6/1990 | Cross ............ A61F 5/455 600/574 |
| 4,950,262 | A | 8/1990 | Takagi |

(56) References Cited

U.S. PATENT DOCUMENTS

| | | | |
|---|---|---|---|
| 4,955,922 A | 9/1990 | Terauchi | |
| 4,957,487 A | 9/1990 | Gerow | |
| 4,965,460 A | 10/1990 | Tanaka et al. | |
| 4,986,823 A | 1/1991 | Anderson et al. | |
| 4,987,849 A | 1/1991 | Sherman | |
| 5,002,541 A * | 3/1991 | Conkling | A61F 5/44 |
| | | | 604/324 |
| 5,004,463 A | 4/1991 | Nigay | |
| 5,031,248 A | 7/1991 | Kemper | |
| 5,045,077 A | 9/1991 | Blake | |
| 5,045,283 A | 9/1991 | Patel | |
| 5,049,144 A | 9/1991 | Payton | |
| 5,053,339 A | 10/1991 | Patel | |
| 5,057,092 A | 10/1991 | Webster | |
| 5,058,088 A | 10/1991 | Haas et al. | |
| 5,071,347 A | 12/1991 | Mcguire | |
| 5,078,707 A | 1/1992 | Peter | |
| 5,084,037 A | 1/1992 | Barnett | |
| 5,100,396 A | 3/1992 | Zamierowski | |
| 5,112,324 A | 5/1992 | Wallace | |
| 5,147,301 A | 9/1992 | Ruvio | |
| 5,176,667 A | 1/1993 | Debring | |
| 5,195,997 A | 3/1993 | Carns | |
| 5,196,654 A | 3/1993 | Diflora et al. | |
| 5,203,699 A | 4/1993 | Mcguire | |
| 5,244,458 A | 9/1993 | Takasu | |
| 5,246,454 A | 9/1993 | Peterson | |
| 5,267,988 A | 12/1993 | Farkas | |
| 5,275,307 A | 1/1994 | Freese | |
| 5,282,795 A | 2/1994 | Finney | |
| 5,294,983 A | 3/1994 | Ersoz et al. | |
| 5,295,983 A | 3/1994 | Kubo | |
| 5,300,052 A | 4/1994 | Kubo | |
| 5,304,749 A | 4/1994 | Crandell | |
| 5,312,383 A | 5/1994 | Kubalak | |
| 5,318,550 A | 6/1994 | Cermak et al. | |
| 5,330,459 A | 7/1994 | Lavon et al. | |
| 5,334,174 A * | 8/1994 | Street | A61F 5/451 |
| | | | 604/315 |
| 5,340,840 A | 8/1994 | Park et al. | |
| 5,382,244 A | 1/1995 | Telang | |
| 5,409,014 A | 4/1995 | Napoli et al. | |
| 5,411,495 A | 5/1995 | Willingham | |
| 5,423,784 A | 6/1995 | Metz | |
| 5,456,246 A | 10/1995 | Schmieding et al. | |
| 5,466,229 A | 11/1995 | Elson et al. | |
| 5,478,334 A | 12/1995 | Bernstein | |
| 5,499,977 A | 3/1996 | Marx | |
| 5,543,042 A | 8/1996 | Filan et al. | |
| D373,928 S | 9/1996 | Green | |
| 5,582,604 A | 12/1996 | Ahr et al. | |
| 5,592,950 A | 1/1997 | Kopelowicz | |
| 5,605,161 A | 2/1997 | Cross | |
| 5,618,277 A | 4/1997 | Goulter | |
| 5,628,735 A | 5/1997 | Skow | |
| 5,636,643 A | 6/1997 | Argenta et al. | |
| 5,637,104 A | 6/1997 | Ball et al. | |
| 5,674,212 A | 10/1997 | Osborn et al. | |
| 5,678,564 A | 10/1997 | Lawrence et al. | |
| 5,678,654 A | 10/1997 | Uzawa | |
| 5,681,297 A * | 10/1997 | Hashimoto | A61F 5/451 |
| | | | 119/164 |
| 5,687,429 A | 11/1997 | Rahlff | |
| 5,695,485 A | 12/1997 | Duperret et al. | |
| 5,700,254 A | 12/1997 | Mcdowall et al. | |
| 5,701,612 A | 12/1997 | Daneshvar | |
| 5,705,777 A | 1/1998 | Flanigan et al. | |
| 5,752,944 A | 5/1998 | Dann et al. | |
| 5,763,333 A | 6/1998 | Suzuki et al. | |
| 5,772,644 A | 6/1998 | Bark et al. | |
| 5,792,132 A * | 8/1998 | Garcia | A61F 5/451 |
| | | | 604/385.01 |
| 5,827,243 A | 10/1998 | Palestrant | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,859,393 A | 1/1999 | Cummins et al. | |
| 5,865,378 A | 2/1999 | Hollinshead et al. | |
| 5,876,393 A | 3/1999 | Ahr et al. | |
| 5,887,291 A | 3/1999 | Bellizzi | |
| 5,891,125 A | 4/1999 | Plumley | |
| 5,894,608 A | 4/1999 | Birbara | |
| D409,303 S | 5/1999 | Oepping | |
| 5,911,222 A | 6/1999 | Lawrence et al. | |
| 5,957,904 A | 9/1999 | Holland | |
| 5,968,026 A | 10/1999 | Osborn et al. | |
| 5,972,505 A | 10/1999 | Phillips et al. | |
| 6,007,526 A | 12/1999 | Passalaqua et al. | |
| 6,039,060 A | 3/2000 | Rower | |
| 6,050,983 A | 4/2000 | Moore et al. | |
| 6,059,762 A | 5/2000 | Boyer et al. | |
| 6,063,064 A | 5/2000 | Tuckey et al. | |
| 6,098,625 A | 8/2000 | Winkler | |
| 6,105,174 A | 8/2000 | Karlsten et al. | |
| 6,113,582 A | 9/2000 | Dwork | |
| 6,117,163 A | 9/2000 | Bierman | |
| 6,123,398 A | 9/2000 | Arai et al. | |
| 6,129,718 A | 10/2000 | Wada et al. | |
| 6,131,964 A | 10/2000 | Sareshwala | |
| 6,152,902 A | 11/2000 | Christian et al. | |
| 6,164,569 A | 12/2000 | Hollinshead et al. | |
| 6,177,606 B1 | 1/2001 | Etheredge et al. | |
| 6,209,142 B1 | 4/2001 | Mattsson et al. | |
| 6,220,050 B1 | 4/2001 | Cooksey | |
| 6,244,311 B1 | 6/2001 | Hand et al. | |
| 6,248,096 B1 | 6/2001 | Dwork et al. | |
| 6,263,887 B1 | 7/2001 | Dunn | |
| 6,283,246 B1 | 9/2001 | Nishikawa | |
| 6,311,339 B1 | 11/2001 | Kraus | |
| 6,336,919 B1 | 1/2002 | Davis et al. | |
| 6,338,729 B1 | 1/2002 | Wada et al. | |
| 6,352,525 B1 | 3/2002 | Wakabayashi | |
| 6,394,988 B1 * | 5/2002 | Hashimoto | A61G 9/00 |
| | | | 604/327 |
| 6,398,742 B1 | 6/2002 | Kim | |
| 6,406,463 B1 | 6/2002 | Brown | |
| 6,409,712 B1 | 6/2002 | Dutari et al. | |
| 6,416,500 B1 | 7/2002 | Wada et al. | |
| 6,423,045 B1 | 7/2002 | Wise et al. | |
| 6,428,522 B1 | 8/2002 | Dipalma et al. | |
| 6,446,454 B1 | 9/2002 | Lee et al. | |
| 6,475,198 B1 | 11/2002 | Lipman et al. | |
| 6,479,726 B1 | 11/2002 | Cole et al. | |
| 6,491,673 B1 | 12/2002 | Palumbo et al. | |
| 6,508,794 B1 | 1/2003 | Palumbo et al. | |
| 6,524,292 B1 | 2/2003 | Dipalma et al. | |
| 6,540,729 B1 | 4/2003 | Wada et al. | |
| 6,547,771 B2 | 4/2003 | Robertson et al. | |
| 6,569,133 B2 | 5/2003 | Cheng et al. | |
| D476,518 S | 7/2003 | Doppelt | |
| 6,592,560 B2 | 7/2003 | Snyder et al. | |
| 6,610,038 B1 | 8/2003 | Dipalma et al. | |
| 6,618,868 B2 | 9/2003 | Minnick | |
| 6,620,142 B1 | 9/2003 | Flueckiger | |
| 6,629,651 B1 | 10/2003 | Male et al. | |
| 6,635,038 B2 | 10/2003 | Scovel | |
| 6,652,495 B1 | 11/2003 | Walker | |
| 6,666,850 B1 | 12/2003 | Ahr et al. | |
| 6,685,684 B1 | 2/2004 | Falconer | |
| 6,695,828 B1 | 2/2004 | Dipalma et al. | |
| 6,699,174 B1 | 3/2004 | Bennett | |
| 6,700,034 B1 | 3/2004 | Lindsay et al. | |
| 6,702,793 B1 | 3/2004 | Sweetser et al. | |
| 6,706,027 B2 | 3/2004 | Harvie et al. | |
| 6,732,384 B2 | 5/2004 | Scott | |
| 6,736,977 B1 | 5/2004 | Hall et al. | |
| 6,740,066 B2 | 5/2004 | Wolff et al. | |
| 6,764,477 B1 | 7/2004 | Chen et al. | |
| 6,783,519 B2 | 8/2004 | Samuelsson | |
| 6,796,974 B2 | 9/2004 | Palumbo et al. | |
| 6,814,547 B2 | 11/2004 | Childers et al. | |
| 6,849,065 B2 | 2/2005 | Schmidt et al. | |
| 6,857,137 B2 | 2/2005 | Otto | |

(56) References Cited

U.S. PATENT DOCUMENTS

| | | |
|---|---|---|
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,122,023 B1* | 10/2006 | Hinoki .............. A61F 13/47254 |
| | | 604/383 |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,171,699 B2 | 2/2007 | Ernest et al. |
| 7,171,871 B2 | 2/2007 | Kozak |
| 7,179,951 B2 | 2/2007 | Krishnaswamy-mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,511 B2 | 6/2009 | Marocco |
| 7,549,512 B2 | 6/2009 | Newberry |
| 7,585,293 B2 | 9/2009 | Vermaak |
| 7,588,560 B1 | 9/2009 | Dunlop |
| 7,637,905 B2 | 12/2009 | Saadat et al. |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,343,125 B2 | 1/2013 | Kawazoe et al. |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2* | 10/2013 | Wada .................... A61F 5/4401 |
| | | 604/361 |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,586,583 B2 | 11/2013 | Hamblin et al. |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,402,424 B2 | 8/2016 | Roy |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |

(56) References Cited

U.S. PATENT DOCUMENTS

| | | |
|---|---|---|
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | McGirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| 10,258,517 B1 | 4/2019 | Maschino et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,500,108 B1 | 12/2019 | Maschino et al. |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 | 6/2021 | Harvie |
| 11,027,900 B2 | 6/2021 | Liu |
| D928,946 S | 8/2021 | Sanchez et al. |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |
| 11,207,206 B2 | 12/2021 | Sharma et al. |
| 11,226,376 B2 | 1/2022 | Yamauchi et al. |
| 11,253,389 B2 | 2/2022 | Sharma et al. |
| 11,253,407 B2 | 2/2022 | Miao et al. |
| 11,326,586 B2 | 5/2022 | Milner et al. |
| 11,369,508 B2 | 6/2022 | Ecklund et al. |
| 11,369,524 B2 | 6/2022 | Hubbard et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,389,318 B2 | 7/2022 | Radl et al. |
| 11,395,871 B2 | 7/2022 | Radl et al. |
| 11,399,990 B2 | 8/2022 | Suyama |
| 11,426,303 B2 | 8/2022 | Davis et al. |
| 11,504,265 B2 | 11/2022 | Godinez et al. |
| 11,529,252 B2 * | 12/2022 | Glithero ............... A61F 5/453 |
| 11,547,788 B2 | 1/2023 | Radl et al. |
| 11,806,266 B2 | 11/2023 | Sanchez et al. |
| 11,839,567 B2 | 12/2023 | Davis et al. |
| D1,010,109 S | 1/2024 | Ecklund et al. |
| 11,857,716 B2 | 1/2024 | Lee et al. |
| 11,865,030 B2 | 1/2024 | Davis et al. |
| 11,890,221 B2 | 2/2024 | Ulreich et al. |
| 11,925,575 B2 | 3/2024 | Newton |
| 11,938,053 B2 | 3/2024 | Austermann et al. |
| 11,944,740 B2 | 4/2024 | Hughett et al. |
| 12,023,457 B2 | 7/2024 | Mann et al. |
| 12,042,422 B2 | 7/2024 | Davis et al. |
| D1,038,385 S | 8/2024 | Ecklund et al. |
| 12,090,083 B2 | 9/2024 | Ecklund et al. |
| 2001/0037097 A1 | 11/2001 | Cheng et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0091364 A1 * | 7/2002 | Prabhakar ............... A61F 5/451 604/327 |
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 * | 10/2003 | Harvie ................... A61F 5/455 604/355 |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 * | 7/2004 | Easter ................... A61F 5/451 604/322 |
| 2004/0147863 A1 | 7/2004 | Diaz et al. |
| 2004/0147894 A1 | 7/2004 | Mizutani et al. |
| 2004/0158221 A1 | 8/2004 | Mizutani et al. |
| 2004/0176731 A1 * | 9/2004 | Cheng ................... A61F 5/455 604/329 |
| 2004/0176746 A1 * | 9/2004 | Forral ................... A61F 5/453 604/544 |
| 2004/0191919 A1 | 9/2004 | Unger et al. |
| 2004/0200936 A1 | 10/2004 | Opperthauser |
| 2004/0207530 A1 | 10/2004 | Nielsen |
| 2004/0236292 A1 * | 11/2004 | Tazoe ................... A61F 5/451 604/317 |
| 2004/0243075 A1 | 12/2004 | Harvie |
| 2004/0254547 A1 * | 12/2004 | Okabe ................... A61F 5/455 604/317 |
| 2005/0010182 A1 | 1/2005 | Parks et al. |
| 2005/0010197 A1 * | 1/2005 | Lau ........................ A61M 1/80 606/1 |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |

(56) References Cited

U.S. PATENT DOCUMENTS

| | | |
|---|---|---|
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1* | 4/2006 | Kay ................... A61F 5/4405 604/328 |
| 2006/0111648 A1 | 5/2006 | Vermaak |
| 2006/0155214 A1 | 7/2006 | Wightman |
| 2006/0171997 A1 | 8/2006 | Gruenbacher et al. |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1* | 10/2009 | Medeiros ................ A61F 5/451 604/347 |
| 2009/0281510 A1 | 11/2009 | Fisher |
| 2009/0283982 A1 | 11/2009 | Thomas |
| 2010/0004612 A1 | 1/2010 | Thevenin |
| 2010/0058660 A1 | 3/2010 | Williams |
| 2010/0121289 A1 | 5/2010 | Parks et al. |
| 2010/0137819 A1* | 6/2010 | Wada ...................... A61F 5/451 604/385.01 |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0145993 A1* | 6/2011 | Rader ...................... A61G 7/02 5/604 |
| 2011/0152802 A1* | 6/2011 | DiCamillo ............. A61F 5/455 604/347 |
| 2011/0164147 A1 | 7/2011 | Takahashi et al. |
| 2011/0172620 A1 | 7/2011 | Khambatta |
| 2011/0172625 A1* | 7/2011 | Wada ...................... A61F 13/42 604/385.01 |
| 2011/0202024 A1 | 8/2011 | Cozzens |
| 2011/0238023 A1* | 9/2011 | Slayton ................ A61F 13/472 604/329 |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1* | 11/2011 | Mitsui ................... A61F 5/4405 604/385.01 |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1* | 10/2012 | Suzuki .................... A61F 13/42 374/45 |
| 2012/0271259 A1* | 10/2012 | Ulert ...................... A61M 1/74 604/327 |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0036544 A1* | 2/2013 | Lee ........................ A61G 9/003 4/443 |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0150813 A1 | 6/2013 | Gordon et al. |

(56) References Cited

U.S. PATENT DOCUMENTS

| | | |
|---|---|---|
| 2013/0218112 A1 | 8/2013 | Thompson |
| 2013/0245586 A1 | 9/2013 | Jha |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0101007 A1* | 4/2016 | Onoda ............... A61G 7/02 604/326 |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1* | 12/2016 | Sanchez ............... A61F 5/453 604/319 |
| 2017/0007438 A1 | 1/2017 | Harvie |
| 2017/0014560 A1 | 1/2017 | Minskoff et al. |
| 2017/0100276 A1* | 4/2017 | Joh ............... A61F 5/455 |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1 | 8/2018 | Davis et al. |
| 2018/0256384 A1* | 9/2018 | Kasirye ............... A61F 5/449 |
| 2018/0271694 A1 | 9/2018 | Fernandez et al. |
| 2018/0280189 A1* | 10/2018 | Kaufman ............... B64G 6/00 |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133814 A1 | 5/2019 | Tammen et al. |
| 2019/0142624 A1* | 5/2019 | Sanchez ............... A61F 5/453 604/319 |
| 2019/0224036 A1 | 7/2019 | Sanchez et al. |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1* | 2/2020 | Godinez ............... A61F 5/451 |
| 2020/0055638 A1 | 2/2020 | Lau et al. |
| 2020/0070392 A1 | 3/2020 | Huber et al. |
| 2020/0085609 A1* | 3/2020 | Schelch ............... A61F 5/4405 |
| 2020/0085610 A1 | 3/2020 | Cohn et al. |
| 2020/0086090 A1 | 3/2020 | Von Weymarn-Schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0206015 A1* | 7/2020 | Langer ............... A61F 5/451 |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0231343 A1 | 7/2020 | Freedman et al. |
| 2020/0232841 A1 | 7/2020 | Satish et al. |
| 2020/0246172 A1* | 8/2020 | Ho ............... A61F 5/451 |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1* | 10/2020 | Eckert ............... A61F 5/4556 |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1* | 12/2020 | Staali ............... A61M 1/71 |
| 2020/0375810 A1 | 12/2020 | Carlin et al. |
| 2020/0385179 A1 | 12/2020 | McCourt |
| 2020/0390591 A1* | 12/2020 | Glithero ............... A61F 5/455 |
| 2020/0390592 A1 | 12/2020 | Merrill |
| 2020/0405521 A1* | 12/2020 | Glasroe ............... A61F 5/4408 |

(56) References Cited

U.S. PATENT DOCUMENTS

| | | |
|---|---|---|
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0059853 A1 | 3/2021 | Davis et al. |
| 2021/0061523 A1 | 3/2021 | Bytheway |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315727 A1* | 10/2021 | Jiang ................ A61F 5/4408 |
| 2021/0353450 A1* | 11/2021 | Sharma ............... A61F 5/4404 |
| 2021/0361469 A1 | 11/2021 | Liu et al. |
| 2021/0369495 A1* | 12/2021 | Cheng ................ A61F 5/4405 |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031523 A1 | 2/2022 | Pierpoint |
| 2022/0039995 A1 | 2/2022 | Johannes et al. |
| 2022/0047410 A1* | 2/2022 | Walthall .................. A61M 1/73 |
| 2022/0062027 A1 | 3/2022 | Mitchell et al. |
| 2022/0062028 A1 | 3/2022 | Mitchell et al. |
| 2022/0062029 A1* | 3/2022 | Johannes ............ A61F 5/4401 |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1* | 4/2022 | Jones .................... A61M 1/884 |
| 2022/0117773 A1 | 4/2022 | Davis et al. |
| 2022/0117774 A1* | 4/2022 | Meyer .................. A61F 5/455 |
| 2022/0117775 A1 | 4/2022 | Jones et al. |
| 2022/0133524 A1* | 5/2022 | Davis ...................... A61M 1/80 |
| | | 604/319 |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1* | 7/2022 | Johannes .............. A61F 5/451 |
| 2022/0218510 A1* | 7/2022 | Metzger ................ A61F 5/443 |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1* | 9/2022 | Johannes ............... A61F 5/451 |
| 2022/0280357 A1 | 9/2022 | Jagannathan et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1* | 10/2022 | Kriscovich ........... A61F 5/4408 |
| 2022/0331170 A1 | 10/2022 | Erdem et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1* | 11/2022 | Wang .................... A61F 5/4408 |
| 2022/0370234 A1* | 11/2022 | Hughett ................. A61F 5/451 |
| 2022/0370235 A1 | 11/2022 | Johannes et al. |
| 2022/0370237 A1* | 11/2022 | Parmar ................. A61F 5/4401 |
| 2022/0387001 A1 | 12/2022 | Askenazi et al. |
| 2022/0395390 A1 | 12/2022 | Brooks |
| 2022/0395391 A1* | 12/2022 | Saunders .............. A61F 5/4404 |
| 2022/0409422 A1 | 12/2022 | Schneider et al. |
| 2023/0018845 A1 | 1/2023 | Lee |
| 2023/0020563 A1* | 1/2023 | Sharma .................. A61F 5/453 |
| 2023/0031640 A1 | 2/2023 | Hughett et al. |
| 2023/0037159 A1* | 2/2023 | Brennan ................ A61F 5/451 |
| 2023/0052238 A1 | 2/2023 | Oluwasogo |
| 2023/0062944 A1 | 3/2023 | Vollenberg et al. |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1* | 3/2023 | Hughett ................ A61F 5/4404 |
| 2023/0099821 A1 | 3/2023 | Radl et al. |
| 2023/0099991 A1 | 3/2023 | Bianchi et al. |
| 2023/0105001 A1* | 4/2023 | Whittome .......... A61F 13/53708 |
| | | 604/319 |
| 2023/0110577 A1 | 4/2023 | Choi |
| 2023/0138269 A1* | 5/2023 | Abdelal ................ A61F 5/451 |
| | | 604/347 |
| 2023/0145365 A1* | 5/2023 | Martin .................. A61F 5/455 |
| | | 604/347 |
| 2023/0155253 A1 | 5/2023 | Yin et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0041638 A1 | 2/2024 | Johannes et al. |
| 2024/0058161 A1 | 2/2024 | Ulreich et al. |
| 2024/0065881 A1 | 2/2024 | Kuroda et al. |
| 2024/0099874 A1 | 3/2024 | Sanchez et al. |
| 2024/0110318 A1 | 4/2024 | Bendt et al. |
| 2024/0123134 A1 | 4/2024 | Kharkar et al. |
| 2024/0261131 A1 | 8/2024 | Garvey et al. |

FOREIGN PATENT DOCUMENTS

| | | |
|---|---|---|
| CA | 2165286 C | 9/1999 |
| CA | 2354132 A1 | 6/2000 |
| CA | 2359091 C | 9/2003 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1434693 A | 8/2003 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |

(56) References Cited

FOREIGN PATENT DOCUMENTS

| | | | |
|---|---|---|---|
| CN | 102159159 A | 8/2011 |
| CN | 202184840 U | 4/2012 |
| CN | 102481441 A | 5/2012 |
| CN | 202463712 U | 10/2012 |
| CN | 202950810 U | 5/2013 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 205849719 U | 1/2017 |
| CN | 106726089 A | 5/2017 |
| CN | 107847384 A | 3/2018 |
| CN | 107920912 A | 4/2018 |
| CN | 108420590 A | 8/2018 |
| CN | 209285902 U | 8/2019 |
| CN | 110381883 A | 10/2019 |
| CN | 211198839 U | 8/2020 |
| CN | 112566550 A | 3/2021 |
| CN | 112603184 A | 4/2021 |
| CN | 114007493 A | 2/2022 |
| CN | 114375187 A | 4/2022 |
| CN | 116096332 A | 5/2023 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 102012112818 A1 | 6/2014 |
| DE | 202015104597 U1 | 7/2016 |
| DE | 102020121462 B3 | 1/2022 |
| DK | 9600118 | 11/1996 |
| EP | 0032138 A2 | 7/1981 |
| EP | 0066070 B1 | 12/1982 |
| EP | 0068712 A1 | 1/1983 |
| EP | 0140470 A1 | 5/1985 |
| EP | 0140471 B1 | 5/1988 |
| EP | 0274753 A2 | 7/1988 |
| EP | 0119143 B1 | 11/1988 |
| EP | 0483592 A1 | 5/1992 |
| EP | 0610638 A1 | 8/1994 |
| EP | 0613355 A1 | 9/1994 |
| EP | 0613355 B1 | 1/1997 |
| EP | 0787472 A1 | 8/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3753492 A1 | 12/2020 |
| EP | 3788992 A1 | 3/2021 |
| EP | 3576689 B1 | 3/2022 |
| EP | 3752110 B1 | 3/2022 |
| EP | 3787570 B1 | 3/2022 |
| EP | 4025163 A1 | 7/2022 |
| EP | 3463180 B1 | 3/2023 |
| EP | 3569205 B1 | 6/2023 |
| EP | 4382082 A2 | 6/2024 |
| GB | 871820 A | 7/1961 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2181953 A | 5/1987 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| GB | 2612752 A | 5/2023 |
| IT | 201800009129 A1 | 4/2020 |
| JP | S498638 U | 1/1974 |
| JP | S5410596 A | 1/1979 |
| JP | S5410596 Y2 | 5/1979 |
| JP | S54155729 U | 10/1979 |
| JP | S55155618 A | 12/1980 |
| JP | S56152629 U | 11/1981 |
| JP | S57142534 U | 9/1982 |
| JP | S5888596 U | 6/1983 |
| JP | S58188016 U | 12/1983 |
| JP | S63107780 U | 7/1988 |
| JP | H0267530 A | 3/1990 |
| JP | H02103871 A | 4/1990 |
| JP | H02131422 A | 5/1990 |
| JP | H02131422 U | 11/1990 |
| JP | H0460220 A | 2/1992 |
| JP | H05123349 A | 5/1993 |
| JP | H05123350 A | 5/1993 |
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2001054531 A | 2/2001 |
| JP | 2001070331 A | 3/2001 |
| JP | 2001224616 A * | 8/2001 |
| JP | 2001276107 A | 10/2001 |
| JP | 2001276108 A | 10/2001 |
| JP | 2002028173 A | 1/2002 |
| JP | 2003038563 A | 2/2003 |
| JP | 2003505152 A | 2/2003 |
| JP | 2003126242 A | 5/2003 |
| JP | 2003180722 A | 7/2003 |
| JP | 2003528691 A | 9/2003 |
| JP | 2004057578 A | 2/2004 |
| JP | 2004130056 A | 4/2004 |
| JP | 2004267530 A | 9/2004 |
| JP | 2005052219 A | 3/2005 |
| JP | 2005066011 A | 3/2005 |
| JP | 2005066325 A | 3/2005 |
| JP | 2005102978 A | 4/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 2007209687 A | 8/2007 |
| JP | 4039641 B2 | 11/2007 |
| JP | 2008005975 A | 1/2008 |
| JP | 2009509570 A | 3/2009 |
| JP | 2009165887 A | 7/2009 |
| JP | 2009525776 A | 7/2009 |
| JP | 2010504150 A | 2/2010 |

(56) References Cited

FOREIGN PATENT DOCUMENTS

| | | | |
|---|---|---|---|
| JP | 2010081981 A | 4/2010 | |
| JP | 4640772 B2 | 12/2010 | |
| JP | 2010536439 A | 12/2010 | |
| JP | 2011500225 A | 1/2011 | |
| JP | 2011030962 A | 2/2011 | |
| JP | 4747166 B2 | 5/2011 | |
| JP | 2011087823 A | 5/2011 | |
| JP | 4801218 B1 | 8/2011 | |
| JP | 2011218130 A | 11/2011 | |
| JP | 2011224070 A | 11/2011 | |
| JP | 3175719 U | 4/2012 | |
| JP | 2012523869 A | 10/2012 | |
| JP | 2013238608 A | 11/2013 | |
| JP | 2014521960 A | 8/2014 | |
| JP | 2015092945 A | 5/2015 | |
| JP | 3198994 B2 | 7/2015 | |
| JP | 2016521191 A | 7/2016 | |
| JP | 2017014698 A | 1/2017 | |
| JP | 2019076342 A | 5/2019 | |
| JP | 2019525811 A | 9/2019 | |
| JP | 2019170942 A | 10/2019 | |
| JP | 2019533492 A | 11/2019 | |
| JP | 2021120686 A | 8/2021 | |
| JP | 2021522009 A | 8/2021 | |
| JP | 2021522013 A | 8/2021 | |
| JP | 7129493 B2 | 8/2022 | |
| JP | 2023532132 A | 7/2023 | |
| KR | 200290061 Y1 | 9/2002 | |
| KR | 20030047451 A | 6/2003 | |
| KR | 20140039485 A | 4/2014 | |
| KR | 101432639 B1 | 8/2014 | |
| KR | 20180106659 A | 10/2018 | |
| KR | 20180108774 A | 10/2018 | |
| SE | 505542 C2 | 9/1997 | |
| WO | 8101957 A1 | 7/1981 | |
| WO | 8804558 A1 | 6/1988 | |
| WO | 9104714 A2 | 4/1991 | |
| WO | 9104714 A3 | 6/1991 | |
| WO | 9220299 A3 | 2/1993 | |
| WO | WO-9307839 A1 * | 4/1993 | ............ A61F 5/451 |
| WO | 9309736 A2 | 5/1993 | |
| WO | 9309736 A3 | 6/1993 | |
| WO | 9514448 A2 | 6/1995 | |
| WO | 9600096 A1 | 1/1996 | |
| WO | 9634636 A1 | 11/1996 | |
| WO | 9817211 A1 | 4/1998 | |
| WO | 9830336 A1 | 7/1998 | |
| WO | 0000112 A1 | 1/2000 | |
| WO | 0000113 A1 | 1/2000 | |
| WO | 0025651 A1 | 5/2000 | |
| WO | 0033773 A1 | 6/2000 | |
| WO | 0057784 A1 | 10/2000 | |
| WO | WO-0069377 A1 * | 11/2000 | ............ A41B 13/04 |
| WO | 0079497 A1 | 12/2000 | |
| WO | 0145618 A1 | 6/2001 | |
| WO | 0145621 A1 | 6/2001 | |
| WO | 02094160 A1 | 11/2002 | |
| WO | 03013967 A1 | 2/2003 | |
| WO | 03024824 A1 | 3/2003 | |
| WO | 03055423 A1 | 7/2003 | |
| WO | 03071931 A2 | 9/2003 | |
| WO | 03079942 A1 | 10/2003 | |
| WO | 03071931 A3 | 2/2004 | |
| WO | 2004019836 A1 | 3/2004 | |
| WO | 2004024046 A1 | 3/2004 | |
| WO | 2004026195 A1 | 4/2004 | |
| WO | 2005051252 A1 | 6/2005 | |
| WO | 2005074571 A3 | 9/2005 | |
| WO | 2005089687 A2 | 9/2005 | |
| WO | 2005107661 A2 | 11/2005 | |
| WO | 2006021220 A1 | 3/2006 | |
| WO | 2006037140 A2 | 4/2006 | |
| WO | 2007005851 A2 | 1/2007 | |
| WO | 2007007845 A1 | 1/2007 | |
| WO | 2007042823 A2 | 4/2007 | |
| WO | 2007055651 A1 | 5/2007 | |
| WO | 2006098950 A3 | 11/2007 | |
| WO | 2007128156 A3 | 2/2008 | |
| WO | 2008026106 A2 | 3/2008 | |
| WO | 2008078117 A1 | 7/2008 | |
| WO | 2008104019 A1 | 9/2008 | |
| WO | 2008141471 A1 | 11/2008 | |
| WO | 2009004368 A1 | 1/2009 | |
| WO | 2009004369 A1 | 1/2009 | |
| WO | 2009052496 A1 | 4/2009 | |
| WO | WO-2009052502 A1 * | 4/2009 | ............ A61B 5/445 |
| WO | 2009007702 A4 | 7/2009 | |
| WO | 2009101738 A1 | 8/2009 | |
| WO | 2010058192 A1 | 5/2010 | |
| WO | 2010030122 A3 | 7/2010 | |
| WO | 2010101915 A3 | 1/2011 | |
| WO | 2011018132 A1 | 2/2011 | |
| WO | 2011018133 A1 | 2/2011 | |
| WO | 2011024864 A1 | 3/2011 | |
| WO | 2011054118 A1 | 5/2011 | |
| WO | 2011079132 A1 | 6/2011 | |
| WO | 2011107972 A1 | 9/2011 | |
| WO | 2011108972 A1 | 9/2011 | |
| WO | 2011117292 A1 | 9/2011 | |
| WO | 2011123219 A1 | 10/2011 | |
| WO | 2011132043 A1 | 10/2011 | |
| WO | 2012012908 A1 | 2/2012 | |
| WO | 2012065274 A1 | 5/2012 | |
| WO | 2012097462 A1 | 7/2012 | |
| WO | 2012098796 A1 | 7/2012 | |
| WO | 2012101288 A1 | 8/2012 | |
| WO | 2012175916 A1 | 12/2012 | |
| WO | 2013018435 A1 | 2/2013 | |
| WO | 2013033429 A1 | 3/2013 | |
| WO | 2013055434 A1 | 4/2013 | |
| WO | 2013082397 A1 | 6/2013 | |
| WO | 2013103291 A2 | 7/2013 | |
| WO | 2013131109 A1 | 9/2013 | |
| WO | 2013167478 A1 | 11/2013 | |
| WO | 2013177716 A1 | 12/2013 | |
| WO | 2014041534 A1 | 3/2014 | |
| WO | 2014046420 A1 | 3/2014 | |
| WO | 2014118518 A1 | 8/2014 | |
| WO | 2014160852 A1 | 10/2014 | |
| WO | 2015023599 A1 | 2/2015 | |
| WO | 2015052348 A1 | 4/2015 | |
| WO | 2015068384 A1 | 5/2015 | |
| WO | 2015169403 A1 | 11/2015 | |
| WO | 2015170307 A1 | 11/2015 | |
| WO | 2015197462 A1 | 12/2015 | |
| WO | 2016051385 A1 | 4/2016 | |
| WO | 2016055989 A1 | 4/2016 | |
| WO | 2016071894 A1 | 5/2016 | |
| WO | 2016103242 A1 | 6/2016 | |
| WO | 2016116915 A1 | 7/2016 | |
| WO | 2016124203 A1 | 8/2016 | |
| WO | 2016139448 A1 | 9/2016 | |
| WO | 2016166562 A1 | 10/2016 | |
| WO | 2016167535 A1 | 10/2016 | |
| WO | 2016191574 A1 | 12/2016 | |
| WO | 2016200088 A1 | 12/2016 | |
| WO | 2016200361 A1 | 12/2016 | |
| WO | 2016204731 A1 | 12/2016 | |
| WO | 2017001532 A2 | 1/2017 | |
| WO | 2017075226 A1 | 5/2017 | |
| WO | 2017152198 A1 | 9/2017 | |
| WO | 2017153357 A1 | 9/2017 | |
| WO | 2017162559 A1 | 9/2017 | |
| WO | 2017205446 A1 | 11/2017 | |
| WO | 2017209779 A1 | 12/2017 | |
| WO | 2017210524 A1 | 12/2017 | |
| WO | 2018022414 A1 | 2/2018 | |
| WO | 2018044781 A1 | 3/2018 | |
| WO | 2018056953 A1 | 3/2018 | |
| WO | 2018090550 A1 | 5/2018 | |
| WO | 2018138513 A1 | 8/2018 | |
| WO | 2018144318 A1 | 8/2018 | |
| WO | 2018144463 A1 | 8/2018 | |
| WO | 2018150263 A1 | 8/2018 | |

(56) References Cited

FOREIGN PATENT DOCUMENTS

| | | |
|---|---|---|
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019041005 A1 | 3/2019 |
| WO | 2019044217 A1 | 3/2019 |
| WO | 2019044218 A1 | 3/2019 |
| WO | 2019044219 A1 | 3/2019 |
| WO | 2019050959 A1 | 3/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212951 A1 | 11/2019 |
| WO | 2019212952 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2019226826 A1 | 11/2019 |
| WO | WO-2019212954 A1 * 11/2019 ........... A61F 13/496 | |
| WO | 2019239433 A1 | 12/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020182923 A1 | 9/2020 |
| WO | 2020204967 A1 | 10/2020 |
| WO | 2020205939 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021046501 A1 | 3/2021 |
| WO | 2021086868 A1 | 5/2021 |
| WO | 2021094352 A1 | 5/2021 |
| WO | 2021094639 A1 | 5/2021 |
| WO | 2021097067 A1 | 5/2021 |
| WO | 2021102296 A1 | 5/2021 |
| WO | 2021107025 A1 | 6/2021 |
| WO | 2021138411 A1 | 7/2021 |
| WO | 2021138414 A1 | 7/2021 |
| WO | 2021154686 A1 | 8/2021 |
| WO | 2021155206 A1 | 8/2021 |
| WO | 2021170075 A1 | 9/2021 |
| WO | 2021173436 A1 | 9/2021 |
| WO | 2021188817 A1 | 9/2021 |
| WO | 2021195384 A1 | 9/2021 |
| WO | 2021205995 A1 | 10/2021 |
| WO | 2021207621 A1 | 10/2021 |
| WO | 2021211568 A1 | 10/2021 |
| WO | 2021211801 A1 | 10/2021 |
| WO | 2021211914 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022051360 A1 | 3/2022 |
| WO | 2022054613 A1 | 3/2022 |
| WO | 2022066704 A1 | 3/2022 |
| WO | 2022067392 A1 | 4/2022 |
| WO | 2022069950 A1 | 4/2022 |
| WO | 2022071429 A1 | 4/2022 |
| WO | 2022076322 A1 | 4/2022 |
| WO | 2022076427 A2 | 4/2022 |
| WO | 2022086898 A1 | 4/2022 |
| WO | 2022090199 A1 | 5/2022 |
| WO | 2022098536 A1 | 5/2022 |
| WO | 2022099087 A1 | 5/2022 |
| WO | 2022101999 A1 | 5/2022 |
| WO | 2022115692 A1 | 6/2022 |
| WO | 2022125685 A1 | 6/2022 |
| WO | 2022140545 A1 | 6/2022 |
| WO | 2022145231 A1 | 7/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022187152 A1 | 9/2022 |
| WO | 2022192188 A1 | 9/2022 |
| WO | 2022192347 A1 | 9/2022 |
| WO | 2022204000 A1 | 9/2022 |
| WO | 2022216507 A1 | 10/2022 |
| WO | 2022216776 A1 | 10/2022 |
| WO | 2022222030 A1 | 10/2022 |
| WO | 2023286058 A1 | 1/2023 |
| WO | 2023014639 A1 | 2/2023 |
| WO | 2023014641 A1 | 2/2023 |
| WO | 2023018475 A2 | 2/2023 |
| WO | 2023023777 A1 | 3/2023 |
| WO | 2023034453 A1 | 3/2023 |
| WO | 2023038945 A1 | 3/2023 |
| WO | 2023038950 A1 | 3/2023 |
| WO | 2023049109 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023191764 A1 | 10/2023 |
| WO | 2023244238 A1 | 12/2023 |
| WO | 2024058788 A1 | 3/2024 |

OTHER PUBLICATIONS

Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.

(56) References Cited

OTHER PUBLICATIONS

Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 2021.
International Search Report and Written Opinion from International Application No. PCT/US2021/027913 mailed Jul. 12, 2021.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/899,956 mailed Oct. 16, 2020.
Non-Final Office Action for U.S. Appl. No. 16/904,868 mailed Nov. 25, 2020.

(56) References Cited

OTHER PUBLICATIONS

Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 17/088,272 mailed Aug. 5, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/478,180 mailed May 25, 2021.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/611,587, filed Jun. 1, 2017.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 29/741,751, filed Jul. 15, 2020.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.

(56) References Cited

OTHER PUBLICATIONS

U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/214,551, filed Jun. 24, 2021.
U.S. Appl. No. 63/214,570, filed Jun. 24, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
Defendant and Counterclaim Plaintiff Sage Products, LLC's Answer, Defenses, and Counterclaims to Plaintiff's Amended Complaint, Nov. 1, 2019.
Memorandum Order, Feb. 2021, 14 pgs.
Sage's Initial Invalidity Contentions Regarding U.S. Appl. No. 8,287,508; U.S. Appl. No. 10,226,375; and U.S. Appl. No. 10,390,989, May 29, 2020, 193 pages.
Sage's Supplemental and Initial Invalidity Contentions Regarding U.S. Pat. No. 8,287,508; U.S. Pat. No. 10,226,375; U.S. Pat. No. 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. No. 8,287,508, U.S. Pat. No. 10,226,375, U.S. Pat. No. 10,390,989, and U.S. Pat. No. 10,376,407, 292 pages.
Boehringer CareDry System—Second Generation for Non-Invasive Urinary Management for Females, Mar. 2021, 3 pgs.
Excerpts from the 508 (U.S. Pat. No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in *PureWick, LLC* v. *Sage Products, LLC*, Case No. 19-1508-MN, Mar. 23, 2020, 6 pages.
Sage's Preliminary Identification of Claim Elements and Proposed Constructions for U.S. Pat. No. 8,287,508, U.S. Pat. No. 10,226,376, U.S. Pat. No. 10,390,989 and U.S. Pat. No. 10,376,407, Case No. 19-1508-MN, 7 pages.
Decision Granting Institution of Inter Partes Review for U.S. Pat. No. 8,287,508, Case No. 2020-01426, Feb. 17, 2021, 39 pages.
Corrected Certificate of Service, Case No. IPR2020-01426, U.S. Pat. No. 8,287,508, 2020, 2 pages.
Declaration of Diane K. Newman Curriculum Vitae, Petition for Interparties Review, 2020, pp. 1-199.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.
"AMXDmax In-Flight Bladder Relief", Omni Medical; Omni Medical Systems, Inc., 2015.
"AMXDX—Advanced Mission Extender Device Brochure", Omni Medical, Omni Brochure—http://www.omnimedicalsys.com/uploads/AMXDFixedWing.pdf, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, Omni Presentation https://www.omnimedicalsys.com/uploads/AMXDmax_HSD.pdf, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology 2005-06", British Department of Health, Nov. 2006, 40 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
Hollister, "Retracted Penis Pouch by Hollister", Vitality Medical.com, https://www.vitalitymedical.com/hollister-retracted-penis-pouch.html last accessed Jun. 24, 2020, 6 pages.
Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Purewick, "Incontinence Relief for Women", Presentation, Sep. 23, 2015, 7 pages.
Pytlik, "Super Absorbent Polymers", University of Buffalo, http://www.courses.sens.buffalo.edu/ce435/Diapers/Diapers.html, accessed on Feb. 17, 2017.
Sachtman, "New Relief for Pilots? It Depends", Wired, https://www.wired.com/2008/05/pilot-relief/, 2008, 2 pages.
Non-Final Office Action for U.S. Appl. No. 17/330,657 mailed Aug. 11, 2021.
Non-Final Office Action for U.S. Appl. No. 17/446,256 mailed Apr. 13, 2023.
Non-Final Office Action for U.S. Appl. No. 17/448,811 mailed Mar. 1, 2023.
Non-Final Office Action for U.S. Appl. No. 17/451,345 mailed Dec. 7, 2022.
Non-Final Office Action for U.S. Appl. No. 17/453,260 mailed Mar. 14, 2023.
Non-Final Office Action for U.S. Appl. No. 17/501,591 mailed Apr. 25, 2023.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
Advisory Action for U.S. Appl. No. 16/245,726 mailed Apr. 19, 2023.

(56) References Cited

OTHER PUBLICATIONS

Advisory Action for U.S. Appl. No. 16/369,676 mailed Mar. 24, 2023.
Advisory Action for U.S. Appl. No. 16/433,773 mailed Feb. 15, 2023.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 17/662,700 mailed Jan. 30, 2023.
Corrected Notice of Allowability for U.S. Appl. No. 17/330,657 mailed Dec. 9, 2021.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/904,868 mailed Mar. 10, 2022.
Final Office Action for U.S. Appl. No. 16/905,400 mailed Dec. 9, 2021.
Final Office Action for U.S. Appl. No. 17/051,399 mailed Mar. 9, 2023.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027917 mailed Aug. 19, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/044107 mailed Dec. 23, 2022.
International Search Report and Written Opinion from International Application No. PCT/US2022/044212 mailed Jan. 20, 2023.
International Search Report and Written Opinion from International Application No. PCT/US2022/044243 mailed Feb. 24, 2023.

(56) References Cited

OTHER PUBLICATIONS

Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 11, 2023.
Non-Final Office Action for U.S. Appl. No. 16/433,773 mailed Apr. 21, 2022.
Non-Final Office Action for U.S. Appl. No. 16/449,039 mailed Apr. 27, 2023.
Non-Final Office Action for U.S. Appl. No. 16/449,039 mailed Dec. 8, 2021.
Non-Final Office Action for U.S. Appl. No. 16/452,145 mailed Mar. 28, 2023.
Non-Final Office Action for U.S. Appl. No. 16/452,145 mailed Sep. 28, 2021.
Non-Final Office Action for U.S. Appl. No. 16/452,258 mailed Apr. 26, 2023.
Non-Final Office Action for U.S. Appl. No. 16/452,258 mailed Sep. 28, 2021.
Non-Final Office Action for U.S. Appl. No. 16/478,180 mailed Dec. 20, 2022.
Non-Final Office Action for U.S. Appl. No. 16/478,180 mailed Oct. 22, 2021.
Non-Final Office Action for U.S. Appl. No. 16/899,956 mailed Sep. 2, 2021.
Non-Final Office Action for U.S. Appl. No. 16/904,868 mailed Mar. 15, 2023.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 17/051,550 mailed Dec. 15, 2022.
Non-Final Office Action for U.S. Appl. No. 17/051,585 mailed Mar. 29, 2023.
Non-Final Office Action for U.S. Appl. No. 17/179,116 mailed Mar. 24, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/662,700 mailed Jul. 22, 2022.
Non-Final Office Action for U.S. Appl. No. 29/741,751 mailed Jan. 18, 2022.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/461,036 mailed Feb. 22, 2023.
Notice of Allowance for U.S. Appl. No. 17/461,036 mailed Oct. 6, 2022.
Notice of Allowance for U.S. Appl. No. 17/662,700 mailed Mar. 28, 2023.
Notice of Allowance for U.S. Appl. No. 17/663,046 mailed Jan. 30, 2023.
Notice of Allowance for U.S. Appl. No. 29/741,751 mailed Jun. 9, 2022.
Restriction Requirement for U.S. Appl. No. 16/433,773 mailed Dec. 7, 2021.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/646,771 mailed Apr. 6, 2023.
Text Messages to Lorena Eckert Re Prototype PureWick Holder dated Apr. 16, 2022.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/384,196, filed Dec. 19, 2016.
U.S. Appl. No. 15/612,325, filed Jun. 2, 2017.
U.S. Appl. No. 16/245,726, filed Jan. 11, 2019.
U.S. Appl. No. 17/394,055, filed Aug. 4, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.

(56) References Cited

OTHER PUBLICATIONS

U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/246,121, filed Mar. 21, 2023.
U.S. Appl. No. 18/247,986, filed Apr. 5, 2023.
U.S. Appl. No. 18/299,788, filed Apr. 13, 2023.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112, filed Apr. 10, 2020.
U.S. Appl. No. 63/047,374, filed Jul. 2, 2020.
U.S. Appl. No. 63/094,646, filed Oct. 21, 2020.
U.S. Appl. No. 63/133,892, filed Jan. 5, 2021.
U.S. Appl. No. 63/138,878, filed Jan. 19, 2021.
U.S. Appl. No. 63/191,558, filed May 21, 2021.
U.S. Appl. No. 63/208,262, filed Jun. 8, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
U.S. Appl. No. 63/308,190, filed Feb. 9, 2022.
"*PureWick Corporation* v. *Sage Products, LLC* Transcripts vol. 1", Mar. 28, 2022, 99 pages.
"*PureWick Corporation* v. *Sage Products, LLC* Transcripts vol. 2", Mar. 29, 2022, 106 pages.
"*PureWick Corporation* v. *Sage Products, LLC* Transcripts vol. 3", Mar. 30, 2022, 115 pages.
"*PureWick Corporation* v. *Sage Products, LLC* Transcripts vol. 4", Mar. 31, 2022, 117 pages.
"*PureWick Corporation* v. *Sage Products, LLC* Transcripts vol. 5", Apr. 1, 2022, 72 pages.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali , "Sustainability Assessment: Seventh Generation Diapers versus gDiapers", The University of Vermont, Dec. 6, 2011, pp. 1-31.

Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hwang , et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
Parness , et al., "A microfabricated wedge-shaped adhesive array displaying gecko-like dynamic adhesion, directionality", J.R. Soc. Interface, 2009, pp. 1223-1232.
Pieper , et al., "An external urine-collection device for women: A clinical trial", Journal of ER Nursing, vol. 20, No. 2, Mar./Apr. 1993, pp. 51-55.
Tsipenyuk , et al., "Use of biomimetic hexagonal surface texture in friction against lubricated skin", Journal of the Royal Society—Interface, 2014, pp. 1-6.
Vinas , "A Solution for an Awkward—But Serious—Subject", http://www.aero-news.net/index.cfm?do=main.textpost&id=69ae2bb1-838b-4098-a7b5-7f1bb2505688 last accessed Feb. 8, 2021, 3 pages.
Advisory Action for U.S. Appl. No. 16/478,180 mailed Sep. 7, 2023.
Advisory Action for U.S. Appl. No. 17/051,550 mailed Sep. 8, 2023.
Final Office Action for U.S. Appl. No. 16/369,676 mailed Aug. 31, 2023.
Final Office Action for U.S. Appl. No. 16/478,180 mailed May 31, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/448,811 mailed Aug. 3, 2023.
Final Office Action for U.S. Appl. No. 17/451,345 mailed May 3, 2023.
Final Office Action for U.S. Appl. No. 17/453,260 mailed Oct. 5, 2023.
Final Office Action for U.S. Appl. No. 17/653,137 mailed Sep. 21, 2023.
Final Office Action for U.S. Appl. No. 17/655,464 mailed Sep. 1, 2023.
International Search Report and Written Opinion from International Application No. PCT/US2022/041688 mailed Nov. 21, 2022.
International Search Report and Written Opinion from International Application No. PCT/US2022/043818 mailed Mar. 24, 2023.
International Search Report and Written Opinion from International Application No. PCT/US2022/044208 mailed May 8, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.

(56) References Cited

OTHER PUBLICATIONS

Non-Final Office Action for U.S. Appl. No. 17/051,399 mailed Aug. 18, 2023.
Non-Final Office Action for U.S. Appl. No. 17/326,980 mailed Jul. 11, 2023.
Non-Final Office Action for U.S. Appl. No. 17/446,654 mailed Sep. 8, 2023.
Non-Final Office Action for U.S. Appl. No. 17/450,864 mailed May 10, 2023.
Non-Final Office Action for U.S. Appl. No. 17/451,354 mailed May 3, 2023.
Non-Final Office Action for U.S. Appl. No. 17/646,771 mailed Jul. 5, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 18/139,523 mailed Aug. 17, 2023.
Non-Final Office Action for U.S. Appl. No. 18/140,751 mailed Sep. 14, 2023.
Notice of Allowance for U.S. Appl. No. 16/245,726 mailed Jul. 6, 2023.
Notice of Allowance for U.S. Appl. No. 17/051,554 mailed Jul. 6, 2023.
Notice of Allowance for U.S. Appl. No. 17/461,036 mailed Jun. 30, 2023.
Notice of Allowance for U.S. Appl. No. 17/662,700 mailed Jul. 28, 2023.
Notice of Allowance for U.S. Appl. No. 18/299,788 mailed Jul. 24, 2023.
Restriction Requirement for U.S. Appl. No. 17/051,600 mailed Sep. 21, 2023.
Restriction Requirement for U.S. Appl. No. 17/645,821 mailed Jul. 12, 2023.
Restriction Requirement for U.S. Appl. No. 17/657,474 mailed Jun. 30, 2023.
U.S. Appl. No. 17/664,487, filed May 23, 2022.
U.S. Appl. No. 18/198,464, filed May 17, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 63/150,640, filed Feb. 18, 2021.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary, "Embed Definition & Meaning", https://www.merriam-webster.com/dictionary/embed last accessed Aug. 3, 2023, 2003.
Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/904,868 mailed Jan. 2, 2024.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/653,137 mailed Dec. 1, 2023.
Advisory Action for U.S. Appl. No. 17/655,464 mailed Dec. 13, 2023.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowance for U.S. Appl. No. 17/326,980 mailed Feb. 8, 2024.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/179,116 mailed Oct. 31, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/450,864 mailed Dec. 28, 2023.
Final Office Action for U.S. Appl. No. 17/451,354 mailed Oct. 30, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,751 mailed Jan. 17, 2024.
Final Office Action for U.S. Appl. No. 18/164,800 mailed Dec. 6, 2023.

(56) References Cited

OTHER PUBLICATIONS

International Search Report and Written Opinion from International Application No. PCT/US2023/018474 mailed Sep. 11, 2023.
International Search Report and Written Opinion from International Application No. PCT/US2023/024805 mailed Dec. 14, 2023.
Issue Notification for U.S. Appl. No. 16/245,726 mailed Oct. 18, 2023.
Issue Notification for U.S. Appl. No. 17/461,036 mailed Oct. 11, 2023.
Issue Notification for U.S. Appl. No. 17/663,046 mailed Dec. 20, 2023.
Non-Final Office Action for U.S. Appl. No. 16/452,145 mailed Nov. 2, 2023.
Non-Final Office Action for U.S. Appl. No. 16/478,180 mailed Nov. 7, 2023.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,600 mailed Jan. 17, 2024.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/451,345 mailed Jan. 17, 2024.
Non-Final Office Action for U.S. Appl. No. 17/453,560 mailed Oct. 16, 2023.
Non-Final Office Action for U.S. Appl. No. 17/645,821 mailed Oct. 25, 2023.
Non-Final Office Action for U.S. Appl. No. 17/653,137 mailed Jan. 18, 2024.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/134,857 mailed Jan. 25, 2024.
Non-Final Office Action for U.S. Appl. No. 18/140,163 mailed Nov. 9, 2023.
Non-Final Office Action for U.S. Appl. No. 18/198,464 mailed Dec. 7, 2023.
Notice of Allowance for U.S. Appl. No. 16/369,676 mailed Nov. 14, 2023.
Notice of Allowance for U.S. Appl. No. 17/051,550 mailed Feb. 7, 2024.
Notice of Allowance for U.S. Appl. No. 17/051,554 mailed Oct. 18, 2023.
Notice of Allowance for U.S. Appl. No. 17/326,980 mailed Jan. 29, 2024.
Notice of Allowance for U.S. Appl. No. 17/453,560 mailed Jan. 31, 2024.
Notice of Allowance for U.S. Appl. No. 17/662,700 mailed Nov. 15, 2023.
Notice of Allowance for U.S. Appl. No. 18/299,788 mailed Nov. 6, 2023.
Restriction Requirement for U.S. Appl. No. 18/134,857 mailed Oct. 23, 2023.
Submission in Opposition Proceedings for European Application No. 17807547.9 filed Jan. 10, 2024.
U.S. Appl. No. 17/451,719, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/681,987, filed Feb. 7, 2024.
U.S. Appl. No. 18/682,006, filed Feb. 7, 2024.
U.S. Appl. No. 63/596,012, filed Nov. 3, 2023.
U.S. Appl. No. 63/608,553, filed Dec. 11, 2023.
Wikipedia Article, "Zylinder (Geometrie)", https://de.wikipedia.org/w/index.php?title=Zylinder_(Geometrie)&oldid=154862081, version of Jun. 1, 2016, 7 pages.
Final Office Action for U.S. Appl. No. 16/433,773 mailed Sep. 9, 2024.
International Search Report and Written Opinion from International Application No. PCT/US2023/085516 mailed Aug. 26, 2024.
Non-Final Office Action for U.S. Appl. No. 17/614,173 mailed Sep. 24, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/653,314 mailed Aug. 29, 2024.
Non-Final Office Action for U.S. Appl. No. 18/584,002 mailed Sep. 19, 2024.
Notice of Allowance for U.S. Appl. No. 16/904,868 mailed Sep. 29, 2024.
Notice of Allowance for U.S. Appl. No. 17/179,116 mailed Sep. 13, 2024.
Notice of Allowance for U.S. Appl. No. 17/450,864 mailed Sep. 18, 2024.
Restriction Requirement for U.S. Appl. No. 17/596,629 mailed Sep. 19, 2024.
Restriction Requirement for U.S. Appl. No. 17/878,268 mailed Sep. 20, 2024.
U.S. Appl. No. 18/828,559, filed Sep. 9, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
Corrected Notice of Allowability for U.S. Appl. No. 17/501,591 mailed Aug. 9, 2024.
Corrected Notice of Allowability for U.S. Appl. No. 17/664,914 mailed Aug. 9, 2024.
Final Office Action for U.S. Appl. No. 17/446,256 mailed Aug. 7, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 18/134,857 mailed Jul. 25, 2024.
International Search Report and Written Opinion from International Application No. PCT/US2023/036238 mailed Jul. 22, 2024.
International Search Report and Written Opinion from International Application No. PCT/US2023/077168 mailed Jun. 24, 2024.
International Search Report and Written Opinion from International Application No. PCT/US2023/080680 mailed Jul. 22, 2024.
Issue Notification for U.S. Appl. No. 17/453,560 mailed Aug. 7, 2024.
Non-Final Office Action for U.S. Appl. No. 16/478,180 mailed Aug. 7, 2024.
Non-Final Office Action for U.S. Appl. No. 17/451,345 mailed Jul. 25, 2024.
Non-Final Office Action for U.S. Appl. No. 17/597,408 mailed Aug. 15, 2024.
Non-Final Office Action for U.S. Appl. No. 17/749,340 mailed Aug. 14, 2024.
Non-Final Office Action for U.S. Appl. No. 17/758,316 mailed Aug. 28, 2024.
Non-Final Office Action for U.S. Appl. No. 18/139,523 mailed Aug. 26, 2024.
Non-Final Office Action for U.S. Appl. No. 18/426,795 mailed Aug. 9, 2024.

(56) References Cited

OTHER PUBLICATIONS

Non-Final Office Action for U.S. Appl. No. 18/451,080 mailed Jul. 30, 2024.
Notice of Allowance for U.S. Appl. No. 17/501,591 mailed Jul. 31, 2024.
Notice of Allowance for U.S. Appl. No. 17/667,067 mailed Aug. 28, 2024.
Notice of Allowance for U.S. Appl. No. 18/140,163 mailed Aug. 21, 2024.
Notice of Allowance for U.S. Appl. No. 18/198,464 mailed Jul. 30, 2024.
Notice of Allowance for U.S. Appl. No. 18/389,009 mailed Aug. 28, 2024.
Restriction Requirement for U.S. Appl. No. 17/625,941 mailed Aug. 7, 2024.
U.S. Appl. No. 17/013,822, filed Sep. 7, 2020.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 63/568,615, filed Mar. 22, 2024.
U.S. Appl. No. 63/683,428, filed Aug. 15, 2024.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/501,591 mailed Feb. 22, 2024.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 16/478,180 mailed Feb. 28, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/645,821 mailed Apr. 3, 2024.
Final Office Action for U.S. Appl. No. 17/808,354 mailed Apr. 10, 2024.
Final Office Action for U.S. Appl. No. 18/140,163 mailed Mar. 27, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077208 mailed May 10, 2024.
Issue Notification for U.S. Appl. No. 16/449,039 mailed Jun. 19, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/326,980 mailed Jul. 10, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/657,474 mailed Jun. 19, 2024.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,258 mailed Jun. 20, 2024.
Non-Final Office Action for U.S. Appl. No. 16/904,868 mailed Mar. 12, 2024.
Non-Final Office Action for U.S. Appl. No. 17/179,116 mailed Feb. 26, 2024.
Non-Final Office Action for U.S. Appl. No. 17/378,015 mailed Jul. 5, 2024.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,673 mailed Mar. 20, 2024.
Non-Final Office Action for U.S. Appl. No. 17/646,771 mailed Apr. 24, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 18/003,029 mailed Mar. 26, 2024.

(56) References Cited

OTHER PUBLICATIONS

Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/389,009 mailed May 24, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 17/326,980 mailed Apr. 5, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/664,914 mailed Jul. 26, 2024.
Notice of Allowance for U.S. Appl. No. 18/198,464 mailed Apr. 17, 2024.
Restriction Requirement for U.S. Appl. No. 17/527,769 mailed Jun. 17, 2024.
Restriction Requirement for U.S. Appl. No. 17/667,097 mailed Mar. 20, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/444,792, filed Aug. 10, 2021.
U.S. Appl. No. 18/249,577, filed Oct. 19, 2021.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 63/561,893, filed Dec. 11, 2023.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (Polyox) in Hydrophilic Matrices", Hydrophilic Matrix Tablets for Oral Controlled Release, AAPS Advances in the Pharmaceutical Sciences vol. 16, 2014, pp. 123-141.
Wikipedia Article, "Decibel", https://web.archive.org/web/20200415219117/https://en.wikipedia.org/wiki/Decibel last accessed Mar. 11, 2024, 21 pages.
Wikipedia Article, "Fiberglass", https://web.archive.org/web/20200309194847/https://en.wikipedia.org/wiki/Fiberglass last accessed Mar. 11, 2024.

\* cited by examiner

FLUID COLLECTION ASSEMBLIES DEFINING WAIST AND LEG OPENINGS

CROSS-REFERENCE FOR RELATED APPLICATION(S)

This application claims priority to U.S. Provisional Patent Application No. 63/064,126 filed on Aug. 11, 2020, the disclosure of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of fluid collection devices continue to seek new and improved devices, systems, and methods to collect urine.

SUMMARY

In an embodiment, a fluid collection assembly is disclosed. The fluid collection assembly including a fluid impermeable barrier at least partially defining a waist opening, two leg openings, and at least one fluid outlet. The fluid collection assembly also including at least one porous material generally conforming to at least a portion the fluid impermeable barrier.

In an embodiment, a fluid collection system is disclosed. The fluid collection assembly including a fluid impermeable barrier at least partially defining a waist opening, two leg openings, and at least one fluid outlet. The fluid collection assembly also including at least one porous material generally conforming to at least a portion the fluid impermeable barrier. The fluid collection system also includes a vacuum source configured to apply a suction force to the fluid collection assembly to withdraw one or more bodily fluids therefrom, a fluid storage container, and at least one conduit coupled to and extends between the at least one fluid outlet, the vacuum source, and the fluid storage container.

In an embodiment, a method of using a fluid collection assembly is disclosed. The method including receiving bodily fluids from an individual wearing the fluid collection assembly into at least one porous material of the fluid collection assembly. The fluid collection assembly includes a fluid impermeable barrier at least partially defining a waist opening, two leg openings, and at least one fluid outlet. The fluid collection assembly also includes at least one porous material that generally conforms to at least a portion the fluid impermeable barrier. The method also includes removing at least some of the bodily fluids from the fluid collection assembly.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
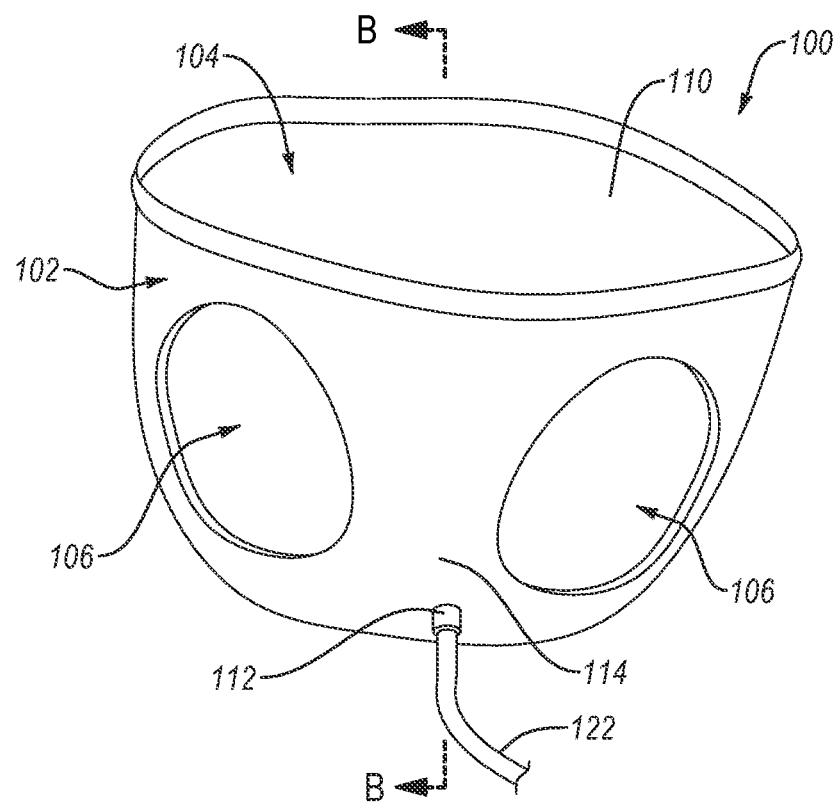
FIG. 1A is an isometric view of a fluid collection assembly, according to an embodiment.

Embodiments disclosed herein are directed to fluid collection assemblies and systems and methods of using the same. An example fluid collection assembly includes a fluid impermeable barrier. The fluid impermeable barrier at least partially defines a waist opening and two leg openings. The waist opening and the two leg openings are configured to have a waist and two legs of an individual positioned therein, respectively. The fluid impermeable barrier also defines at least one fluid outlet. The fluid collection assembly further includes at least one porous material conforming to at least a portion of the fluid impermeable barrier. The porous material may be adjacent to the outlet defined by the fluid impermeable barrier.

The fluid collection assembly is configured to be worn by an individual. When worn by the individual, the fluid collection assembly is positioned on an individual such that the waist and legs of the individual are disposed in the waist opening and the leg openings, respectively. As such, the fluid collection assembly may be worn similar to some underwear (e.g., panties, boxer briefs, etc.). The porous material is positioned on the fluid collection assembly such that the porous material is adjacent to a urethral opening (e.g., vaginal region or penis) when the fluid collection assembly is worn by the individual. Positioning the waist and legs through the waist opening and the leg openings, respectively, represent an improvement over some conventional fluid collection assemblies. For example, some conventional fluid collection assemblies may require the individual to remain substantially still otherwise the convention fluid collection assemblies may become displaced from the urethral opening or required adhesives to applied to the individual which may cause pain when removed. However, disposing the waist and legs of the individual through the waist and leg openings maintains the position of the porous material of the fluid collection assemblies disclosed adjacent to the urethral opening even when the individual moves, such as when the individual changes position (e.g., switches between a standing, sitting, or sitting position), walks, runs, or otherwise moves. Further, the fluid collection assemblies disclosed herein may be able to store more bodily fluids therein compared to such conventional fluid collection assemblies (e.g., conventional fluid collection assemblies that do not define a waist opening and two leg openings).

The porous material may move the bodily fluids away from the urethral opening and towards the fluid outlet such that the bodily fluids may be removed from the fluid collection assembly. Generally, the porous material is formed from a wicking material and does not include an absorbent or adsorbent material since such wicking materials do not store the bodily fluids therein. As such, the wicking material draws the bodily fluids towards the fluid outlet more quickly than if the porous material included an adsorbent or absorbent material thereby allowing the porous material to receive a greater quantity of bodily fluids and at a greater rate of discharge than the adsorbent or absorbent material. Further, the wicking material may decrease the quantity of bodily fluids that are present in the fluid collection assembly a short period of time after the bodily fluids are discharged from the urethral opening thereby maintaining the skin of the individual drier than if the porous material included an adsorbent or absorbent material. The drier skin reduces the likelihood that the fluid collection assembly causes skin degradation (e.g., rashes) and encourages wound healing. However, it is noted that, in some embodiments, the porous material may include at least one adsorbent and/or absorbent material.

As previously discussed, the fluid collection assembly may form part of a system. The additional components of the system allow the system to remove bodily fluids from the fluid collection assembly through the fluid outlet. In other words, unlike conventional fluid collection assemblies such as diapers and pads, the fluid collection assembly is configured to allow and encourages the bodily fluids to flow out of the fluid collection assembly. Removing the bodily fluids from the fluid collection assembly through the fluid outlet allows the fluid collection assembly to receive more bodily fluids that other conventional fluid collection assemblies (e.g., diapers and pads) without needing to be replaced. Further, removing the bodily fluids from the fluid collection assembly allows the skin of the individual to remain drier compared to using the other conventional fluid collection assemblies. In an embodiment, the system may include a vacuum source and a fluid storage container. The vacuum source and the fluid storage container may be coupled to the fluid outlet via at least one conduit. The vacuum source may be configured to apply a suction force that pulls bodily fluids from the porous material and deposits the bodily fluids in the fluid storage container.

Figure 1B:
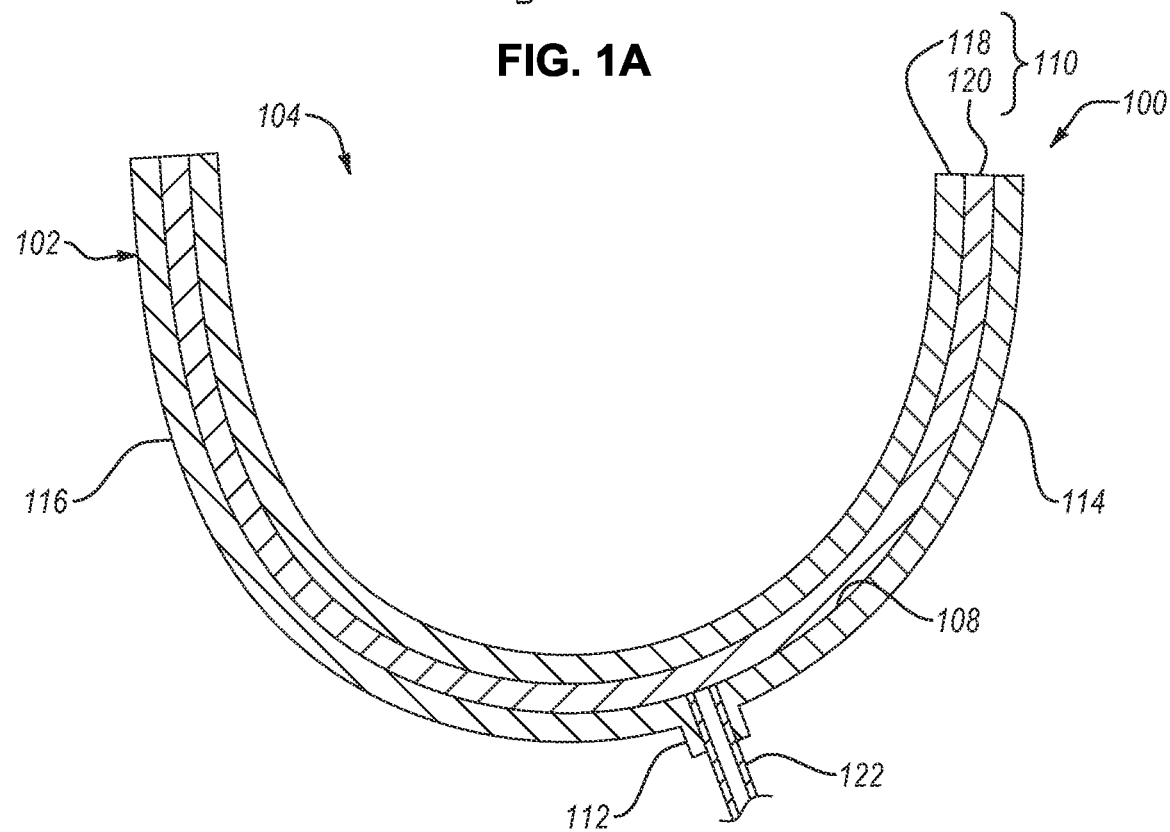
FIG. 1B is a cross-sectional schematic of the fluid collection assembly taken along plane B-B shown in FIG. 1A, according to an embodiment.

FIG. 1A is an isometric view of a fluid collection assembly 100, according to an embodiment. FIG. 1B is a cross-sectional schematic of the fluid collection assembly 100 taken along plane B-B shown in FIG. 1A, according to an embodiment. The fluid collection assembly 100 includes a fluid impermeable barrier 102. The fluid impermeable barrier 102 at least partially defines a waist opening 104 configured to receive a waist of an individual and two leg openings 106 each configured to receive a leg (e.g., thigh) of an individual. The fluid impermeable barrier 102 includes an interior surface 108. The fluid collection assembly 100 includes at least one porous material 110 positioned adjacent to at least a portion of the interior surface 108 of the fluid impermeable barrier 102. The fluid impermeable barrier 102 also includes a fluid outlet 112 and the fluid collection assembly 100 includes a conduit 122 extending from the fluid outlet 112. The fluid outlet 112 and the conduit 122 allow for the removal of bodily fluids received by the porous material 110.

In an embodiment, the fluid impermeable barrier 102 may exhibit a shape that, when worn, is similar to conventionally used underwear that presses against the waist and the legs. For example, the fluid impermeable barrier 102 may exhibit a shape that is similar to boy shorts underwear, traditional briefs, hipsters underwear, thongs, French cut panties, g-strings, control briefs, seamless underwear, Brazilian briefs, bikini panties, boxer briefs, tanga briefs, booty shorts, high waist brief shapers, high cut briefs, hikini panties, jockstraps, long johns, panty girdle, pant liner, skirtkini, sports underwear, pantaloons, trunks, or any other type of underwear.

The fluid impermeable barrier 102 may be formed of any suitable fluid impermeable material(s), such as a fluid impermeable polymer (e.g., silicone, polypropylene, polyethylene, polyethylene terephthalate, a polycarbonate, etc.), a metal film, natural rubber, another suitable material, or combinations thereof. As such, the fluid impermeable barrier 102 substantially prevents the bodily fluids from passing through the fluid impermeable barrier 102. In an example, the fluid impermeable barrier 102 may be air permeable and fluid impermeable. In such an example, the fluid impermeable barrier 102 may be formed of a hydrophobic material that defines a plurality of pores. At least one or more portions of at least an outer surface of the fluid impermeable barrier 102 may be formed from a soft and/or smooth material, thereby reducing chaffing.

The portions of the fluid impermeable barrier 102 that define the waist opening 104 and the two leg openings 106 are configured to contact the waist and legs of an individual using the fluid collection assembly 100. Contacting the waist and legs of the individual with the fluid impermeable barrier 102 may prevent the formation of passageways between the fluid impermeable barrier 102 and the individual through which bodily fluids may leak. For example, the fluid impermeable barrier 102 may contact the waist and legs of the individual even when the individual moves (e.g., walks, runs) substantially without leaking thereby allowing the fluid collection assembly 100 to be used with high mobility individual. However, the shape and size of the waist and/or legs of the individual may vary.

In an embodiment, at least a portion of the fluid impermeable barrier 102 is flexible (e.g., elastic, stretchable) which allows the fluid impermeable barrier 102 to remain in contact with the waist and legs. The flexibility allows the fluid impermeable barrier 102 to substantially continuously remain in contact with a waist and legs of the individual so long as the size of the waist and legs of the individual are the same size or larger than the waist opening 104 and the legs openings 106, respectively. The fluid impermeable barrier 102 is flexible when at least a portion of the fluid impermeable barrier 102 exhibits a percent elongation that is greater than about 5%, greater than about 10%, greater than about 15%, greater than about 20%, greater than about 25%, greater than about 30%, greater than about 40%, greater than about 50%, greater than about 60%, greater than about 70%, greater than about 80%, greater than about 90%, greater than about 100%, or in ranges of about 5% to about 15%, about 10% to about 20%, about 15% to about 25%, about 20% to about 30%, about 25% to about 40%, about 30% to about 50%, about 40% to about 60%, about 50% to about 70%, about 60% to about 80%, about 70% to about 90%, or about 80% to about 100%. Generally, increasing the percent elongation of the fluid impermeable barrier 102 allows the fluid impermeable barrier 102 to accommodate a larger range of sizes of the waist and legs of the individual. However, increasing the percent elongation of the fluid impermeable barrier 102 may allow for a greater likelihood that the fluid impermeable barrier 102 inadvertently stretches to form passageways between the fluid impermeable barrier 102 and the individual thereby possibly permitting leaks. As such, the percent elongation of the fluid impermeable barrier 102 may be selected based on whether the fluid collection assembly 100 is configured to be used with a wide variety of sizes of individuals or to prevent leaks. Examples of material that exhibit such flexibility include, but are not limited to, elastomeric materials and flexible weaves of hydrophobic fabrics.

In an example, at least substantially all of the fluid impermeable barrier 102 is flexible (e.g., formed from a flexible material). In an example, only one or more select regions of the fluid impermeable barrier 102 are flexible. In such an example, the one or more regions of the fluid impermeable barrier 102 that are flexible generally include at least a portion of the fluid impermeable barrier 102 that defines the waist opening 104 and/or at least a portion of the fluid impermeable barrier 102 that defines the leg openings 106. Thus, the portions of the fluid impermeable barrier 102 that defines the waist opening 104 and/or the leg openings 106 may conform to the waist and/or legs disposed therethrough while the rest of the fluid impermeable barrier 102 may be formed from a non-flexible material (e.g., a material exhibiting better fluid impermeability than the flexible material).

In an embodiment, the fluid impermeable barrier 102 may include one or more ruffles (e.g., pleats) formed therein. The ruffles may be formed in one or more regions of the fluid impermeable barrier 102 that defines the waist opening 104 and/or the leg openings 106. The fluid collection assembly 100 may include a flexible material that extends across the one or more ruffles. The flexible material may cause the ruffles to bunch together when in a relaxed state (e.g., no external tensile forces are applied to the fluid impermeable barrier 102). However, a tensile force may be applied to the flexible material, for example, by disposing a waist and/or legs through the waist opening 104 and/or the leg openings 106, respectively, that is larger than the waist opening 104 and/or the leg openings 106. The ruffles may allow the fluid impermeable barrier 102 to be formed from a greater variety of materials (e.g., inflexible materials, materials exhibiting better fluid impermeability and/or better durability than a flexible material, etc.) than if such portions of the fluid impermeable barrier 102 were formed from a flexible material. However, the ruffles may form one or more fluid passageways between each ruffle through which bodily fluids may leak. The leakage of the bodily fluids may be mitigated by configuring the flexible material to pull each gap between the ruffles substantially closed or to provide an absorbent material adjacent to the ruffles. In an embodiment, the fluid impermeable barrier 102 may include the one or more ruffles when the fluid impermeable barrier 102 is formed from flexible material since the ruffles may allow the size of the waist opening 104 and the leg openings 106 to increase more than if the fluid impermeable barrier 102 did not include the ruffles.

In an embodiment, the fluid impermeable barrier 102 may include a slit formed therein that extends from the waist opening 104 to each of the leg openings 106. The slit formed in the fluid impermeable barrier 102 allows the size of the waist opening 104 and the leg openings 106 to be controllably changed depending on the size of the waist and legs disposed through the waist opening 104 and the legs opening 106, respectively. For example, the waist and legs may be disposed through the waist opening 104 and the leg openings 106, respectively, while opposing portions of the fluid impermeable barrier 102 that form the slits ("opposing portions") are spaced from each other. The opposing portions may then be brought together until waist opening 104 and the leg openings 106 contact the waist and legs of the individual, respectively. The opposing portions may then be fixedly secured such that the opposing portions do not move. In an example, fixedly securing the opposing portions includes using string, tape, Velcro, etc. to secure at least one of the opposing portions to another portion of the fluid impermeable barrier 102. In an example, the opposing portions are configured to overlap each other before securing the opposing portions which may prevent leaks between the opposing portions.

The fluid impermeable barrier 102 may include a front portion 114 and a back portion 116. The front portion 114 is configured to generally face the same direction as the abdominal region, mons pubis, and area around the urethral opening (e.g., labia folds, portions of the perineum adjacent to the genitals of the individual, etc.) of the individual when the fluid collection assembly 100 is worn. The back portion 116 is configured to generally face the same direction as the back, buttocks, and portion of the perineum adjacent to the anus of the individual when the fluid collection assembly 100 is worn. In an embodiment, the surface area of the front portion 114 of the fluid impermeable barrier 102 is less than the surface area of the back portion 116 since the surface area of the individual covered by the front portion 114 is smaller than the area of the individual covered by the back portion 116. However, in some embodiments, the front and back surfaces 114, 116 have the same surface area and may be indistinguishable from each other. In an embodiment, the front portion 114 may define a bulge near an intersection of the front portion 114 and the back portion 116 that is configured to receive the testicles of the individual when the fluid collection assembly 100 is configured to be used with male anatomy Referring to FIG. 1B, as previously discussed, the fluid impermeable barrier 102 includes an interior surface 108. The fluid collection assembly 100 includes a porous material 110 disposed adjacent to at least a portion of the interior surface 108. The porous material 110 is disposed adjacent to the portion of the interior surface 108 that is adjacent to the urethral opening of the individual when the fluid collection assembly 100 is used. The portion of the interior surface 108 that is adjacent to the urethral opening of the individual may vary depending on whether the fluid collection assembly 100 is configured to receive bodily fluids from a female urethral opening, male urethral opening, or both. Generally, the portions of the interior surface 108 adjacent to the urethral opening are between the leg openings 106 on the front portion 114 of the fluid impermeable barrier 102. The portions of the interior surface 108 adjacent to a female urethral opening may be closer to an intersection between the front and back portions 114, 116 of the fluid impermeable barrier 102 than portion of the interior surface 108 adjacent to a male urethral opening (e.g., the portions of the interior surface 108 adjacent to the male urethral opening is closer to the waist opening 104). Also, the portion of the interior surface 108 adjacent to a male urethral opening may be greater in size than the portion of the interior surface 108 adjacent to the female urethral opening since the penis may extend outwardly from the individual in a variety of directions and the length of the penis may change.

The porous material 110 may extend from the portion of the interior surface 108 adjacent to the urethral opening to at least the fluid outlet 112. As such, the porous material 110 may channel bodily fluids received thereby towards the fluid outlet 112. The porous material 110 may also extending around the fluid outlet 112 to ensure that the bodily fluids do not inadvertently flow around the fluid outlet 112.

In an embodiment, the porous material 110 may cover other portions of the interior surface 108 in addition to the portions of the interior surface 108 adjacent to the urethral opening, the portions of the interior surface 108 between the portion of the interior surface 108 adjacent to the urethral opening and the fluid outlet 112, and around the fluid outlet 112. For example, the porous material 110 may cover substantially all of the interior surface 108 of the fluid impermeable barrier 102 which may prevent pooling of bodily fluids that where not received by the porous material 110 or left the porous material 110 since pooling of the bodily fluids may damage the skin (e.g., skin degradation), cause discomfort, create unsanitary conditions, and create an odor.

In an embodiment, as previously discussed, the porous material 110 may include a wicking material (e.g., the porous material 110 does not include an adsorbent or absorbent material). The wicking material may be configured to wick any bodily fluids away from the individual and towards the fluid outlet 112. As such, the wicking material may prevent the bodily fluids remaining adjacent to the individual which may cause skin degradation and discomfort, especially since the fluid collection assembly 100 may be configured to be used for prolonged periods of time (e.g., at least 2 hours, at least 3 hours, at least 6 hours, at least 12 hours, at least 18 hours, at least 24 hours, at least 36 hours, about 2 hours to about 6 hours, about 3 hours to about 12 hours, about 6 hours to about 18 hours, about 12 hours to about 24 hours, or about 18 hours to about 36 hours) before being replaced. The permeable properties referred to herein may be wicking, capillary action, diffusion, or other similar properties or processes, and are referred to herein as "permeable" and/or "wicking." Such "wicking" may not include absorption of fluid into the wicking material. Put another way, substantially no absorption of fluid into the material may take place after the material is exposed to the fluid and removed from the fluid for a time. While no absorption is desired, the term "substantially no absorption" may allow for nominal amounts of absorption of fluid into the porous material 110 (e.g., absorbency), such as less than about 30 wt % of the dry weight of the porous material 110, less than about 20 wt %, less than about 15 wt %, less than about 10 wt %, less than about 7 wt %, less than about 5 wt %, less than about 3 wt %, less than about 2 wt %, less than about 1 wt %, or less than about 0.5 wt % of the dry weight of the porous material 110. The porous material 110 may also wick the fluid generally away from an individual, as discussed in more detail below. It is noted that, in some embodiments, the porous material 110 may include an adsorbent or absorbent material instead of or in addition to the wicking material even though such adsorbent or absorbent materials may not remove the bodily fluids from the individual towards the fluid outlet 112 as much as the wicking material. For example, the adsorbent or absorbent materials may impede leaks when the adsorbent or absorbent materials are at the waist opening 104 and/or the leg openings 106.

The porous material 110 may include one or more of a fluid permeable membrane 118 or a fluid permeable support 120. The fluid permeable membrane 118 may be composed to wick fluid away from the individual to the fluid outlet 112, thereby preventing the fluid from leaking while also removing the bodily fluids from the fluid collection assembly 100. The fluid permeable membrane 118 may include any material that may wick the fluid. For example, the fluid permeable membrane 118 may include fabric, such as a gauze (e.g., a silk, linen, or cotton gauze), another soft fabric, or another smooth fabric. Forming the fluid permeable membrane 118 from gauze, soft fabric, and/or smooth fabric may reduce chaffing caused by the fluid collection assembly 100.

The porous material 110 may include the fluid permeable support 120. The fluid permeable support 120 is configured to support the fluid permeable membrane 118 since the fluid permeable membrane 118 may be formed from a relatively foldable, flimsy, or otherwise easily deformable material. For example, the fluid permeable support 120 may be positioned such that the fluid permeable support 120 is disposed between the fluid permeable membrane 118 and the fluid impermeable barrier 102. As such, the fluid permeable support 120 may support and maintain the position of the fluid permeable membrane 118. The fluid permeable support 120 may include any material that may wick the fluid, such as any of the fluid permeable membrane materials disclosed above. For example, the fluid permeable membrane material(s) may be utilized in a more dense or rigid form than in the fluid permeable membrane 118 when used as the fluid permeable support 120. The fluid permeable support 120 may be formed from any fluid permeable material that is less deformable than the fluid permeable membrane 118. For example, the fluid permeable support 120 may include a porous polymer (e.g., nylon, spun nylon fibers, polyester, polyurethane, polyethylene, polypropylene, etc.) structure or an open cell foam. In some examples, the fluid permeable support 120 may be formed from a natural material, such as cotton, wool, silk, or combinations thereof. In such examples, the material may have a coating to prevent or limit absorption of fluid into the material, such as a water repellent coating. In some examples, the fluid permeable support 120 may be formed from fabric, felt, gauze, or combinations thereof. In some examples, the fluid permeable membrane 118 may be optional. For example, the wicking material may include only the fluid permeable support 120. In some examples, the fluid permeable support 120 may be optionally omitted from the fluid collection assembly 100. For example, the wicking material may only include the fluid permeable membrane 118. The fluid permeable support 120 may have a greater ability to wick fluids than the fluid permeable membrane 118. In some examples, the wicking ability of the fluid permeable support 120 and the fluid permeable membrane 118 may be substantially the same.

In an embodiment, the porous material 110 only includes a single layer, such as one of the fluid permeable membrane 118 or the fluid permeable support 120. In an embodiment, the porous material 110 includes three or more layers, such as an odor reducing layer in addition to the fluid permeable membrane 118 and the fluid permeable support 120.

In an embodiment, at least a portion of the porous material 110 (e.g., one or more of the fluid permeable membrane 118 or, more specifically, the fluid permeable support 120) may be hydrophobic. The porous material 110 may be hydrophobic when the porous material 110 exhibits a contact angle with water (a major constituent of bodily fluids) that is greater than about 90°, such as in ranges of about 90° to about 120°, about 105° to about 135°, about 120° to about 150°, about 135° to about 175°, or about 150° to about 180°. The hydrophobicity of the porous material 110 may limit absorption, adsorption, and solubility of the bodily fluids in the porous material 110 thereby decreasing the amount of bodily fluids held in the porous material 110. In an embodiment, at least a portion of the porous material 110 is hydrophobic or hydrophilic. In an embodiment, the fluid permeable support 120 is more hydrophobic (e.g., exhibits a larger contact angle with water) than the fluid permeable membrane 118. The lower hydrophobicity of the fluid permeable membrane 118 may help the porous material 110 receive the bodily fluids from the urethral opening while the hydrophobicity of the fluid permeable support 120 limits the bodily fluids that are retained in the porous material 110.

As previously discussed, the fluid impermeable barrier 102 defines the fluid outlet 112. Generally, the fluid outlet 112 is at or near a gravimetric low point of the fluid collection assembly 100. Locating the fluid outlet 112 at or near a location expected to be the gravimetrically low point of the fluid collection assembly 100 when worn by an individual enables the conduit 122 to receive more of the bodily fluids than if fluid outlet 112 was located elsewhere and reduce the likelihood of pooling (e.g., pooling of the bodily fluids may cause microbe growth and foul odors). For instance, the bodily fluids in the fluid permeable membrane 118 and the fluid permeable support 120 may flow in any direction due to capillary forces. However, the bodily fluids may exhibit a preference to flow in the direction of gravity, especially when at least a portion of the fluid permeable membrane 118 and/or the fluid permeable support 120 is saturated with the bodily fluids. Accordingly, fluid outlet 112 may be located in the fluid collection assembly 100 in a position expected to be the gravimetrically low point in the fluid collection assembly 100 when worn by an individual. The gravimetric low point of the fluid collection assembly 100 may vary depending on the position of the individual. For example, the gravimetric low point of the fluid collection assembly 100 may be at or near the intersection of the front and back portions 114, 116 of the fluid impermeable barrier 102 (e.g., at or near a portion of the fluid impermeable barrier adjacent to a perineum or genitalia of the individual) fluid outlet when the individual is standing, on the back portion 116 near the perineum and/or anus of the individual when the individual is sitting, on the back portion 116 near the anus of the individual or between the anus and waist opening 104 when the individual is laying down on the individual's back, or on the front portion 114 when the individual is laying on the individual's stomach.

The fluid outlet 112 is sized to receive the conduit 122. For example, the fluid outlet 112 may be sized and shaped to form an at least substantially fluid tight seal against the conduit 122 or the at least one tube thereby substantially preventing the bodily fluids from leaking from the fluid collection assembly 100.

The conduit 122 may be used to remove fluid form the fluid collection assembly 100. The conduit 122 (e.g., a tube) includes an inlet and an outlet positioned downstream from the inlet. The outlet may be operably coupled to a suction source, such as a vacuum pump for withdrawing fluid from the fluid collection assembly 100 through the conduit 122. For example, the conduit 122 may extend into the fluid impermeable barrier 102. The conduit 122 fluidly couples the fluid collection assembly 100 with the fluid storage container (not shown) or the vacuum source (not shown).

The conduit 122 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 122 may include silicon or latex. In some examples, the conduit 122 may include one or more portions that are resilient, such as to by having one or more of a diameter or wall thickness that allows the conduit to be flexible.

In an example, the conduit 122 is configured to be at least insertable to be adjacent to the porous material 110. In such an example, the conduit 122 may include one or more markers (not shown) on an exterior thereof that are located to facilitate insertion of the conduit 122 into the fluid outlet 112. For example, the conduit 122 may include one or more markings thereon that are configured to prevent over or under insertion of the conduit 122. In another example, the conduit 122 may include one or more markings thereon that are configured to facilitate correct rotation of the conduit 122. The one or more markings may include a line, a dot, a sticker, or any other suitable marking.

In an embodiment, the fluid collection assembly 100 is configured to be washable. The fluid collection assembly 100 is washable when the components of the fluid collection assembly 100 (e.g., the fluid impermeable barrier 102 and the porous material 110) may be washed substantially without damaging the components of the fluid collection assembly 100. For example, the components of the fluid collection assembly 100 may be configured to not be softened or dissolved in water and may remain attached to each other during the tumbling and spinning cycles of the washing machine. Allowing the fluid collection assembly 100 to be washable allows the fluid collection assembly 100 to be reused which makes using the fluid collection assembly 100 more economical to use and reduces waste. Further, the fluid collection assembly 100 may be machine dryable. The fluid collection assembly 100 is machine dryable when the fluid collection assembly 100 may be spun in the clothes drier at temperature of about 135° C. substantially without damage. In an embodiment, the fluid collection assembly 100 is configured for single use. While a fluid collection assembly 100 configured for single use may increase waste, it allows the fluid collection assembly 100 to be manufactured from a wider range of materials.

Figure 1C:
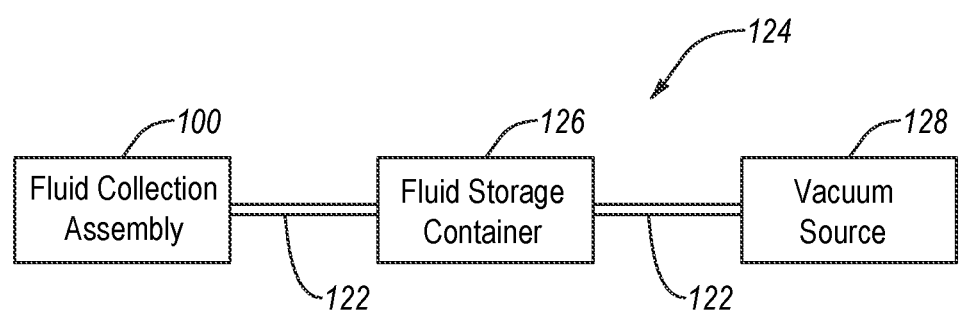
FIG. 1C is a block diagram of a fluid collection system for fluid collection, according to an embodiment.

FIG. 1C is a block diagram of a fluid collection system 124 for fluid collection, according to an embodiment. The fluid collection system 124 includes a fluid collection assembly 100, a fluid storage container 126, and a vacuum source 128. The fluid collection assembly 100, the fluid storage container 126, and the vacuum source 128 may be fluidly coupled to each other via one or more conduits 122. For example, fluid collection assembly 100 may be operably coupled to one or more of the fluid storage container 126 or the vacuum source 128 via the conduit 122. Bodily fluids collected in the fluid collection assembly 100 may be removed from the fluid collection assembly 100 via the conduit 122. Suction force may be introduced into the fluid collection assembly 100 via the inlet of the conduit 122 responsive to suction (e.g., vacuum) force applied at the outlet of the conduit 122.

The suction force may be applied to the outlet of the conduit 122 by the vacuum source 128 either directly or indirectly. The suction force may be applied indirectly via the fluid storage container 126. For example, the outlet of the conduit 122 may be disposed within the fluid storage container 126 and an additional conduit 122 may extend from the fluid storage container 126 to the vacuum source 128. Accordingly, the vacuum source 128 may apply suction to the fluid collection assembly 100 via the fluid storage container 126. The suction force may be applied directly via the vacuum source 128. For example, the outlet of the conduit 122 may be disposed within the vacuum source 128. An additional conduit 122 may extend from the vacuum source 128 to a point outside of the fluid collection assembly 100, such as to the fluid storage container 126. In such examples, the vacuum source 128 may be disposed between the fluid collection assembly 100 and the fluid storage container 126.

The fluid storage container 126 is sized and shaped to retain a fluid therein. The fluid storage container 126 may include a bag (e.g., drainage bag), a bottle or cup (e.g., collection jar), or any other enclosed container for storing bodily fluids such as urine. In some examples, the conduit 122 may extend from the fluid collection assembly 100 and attach to the fluid storage container 126 at a first point therein. An additional conduit 122 may attach to the fluid storage container 126 at a second point thereon and may extend and attach to the vacuum source 128. Accordingly, a vacuum (e.g., suction) may be drawn through the fluid collection assembly 100 via the fluid storage container 126. Bodily fluids, such as urine, may be drained from the fluid collection assembly 100 using the vacuum source 128.

The vacuum source 128 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 128 may provide a vacuum or suction to remove fluid from the fluid collection assembly 100. In an example, the vacuum source 128 may be powered by one or more of a power cord (e.g., connected to a power socket), one or more batteries, or even manual power (e.g., a hand operated vacuum pump). In an example, the vacuum source 128 may be sized and shaped to fit outside of, on, or within the fluid collection assembly 100. In an example, the vacuum source 128 may include one or more miniaturized pumps or one or more micro pumps. The vacuum source 128 disclosed herein may include one or more of a switch, a button, a plug, a remote, or any other device suitable to activate the vacuum source 128.

Referring back to FIGS. 1A and 1B, the fluid collection assembly 100 includes the porous material 110 adjacent to the interior surface 108 of the fluid impermeable barrier 102 such that there are no substantially unoccupied spaces between the porous material 110 and the interior surface 108. The lack of an occupied spaced between the interior surface 108 and the porous material 110 may inhibit pooling of the bodily fluids between the interior surface 108 and the porous material 110. Further, as will be discussed in more detail below, the lack of an unoccupied space between the interior surface 108 and the porous material 110 may allow the fluid collection assembly 100 to be worn more discretely and/or increase the volume of the porous material 110. In an example, at least a significant portion of a surface of the porous material 110 that faces the interior surface 108 of the fluid impermeable barrier 102 and the interior surface 108 are attached together to inhibit the porous material 110 becoming spaced from the interior surface 108. In an example, the porous material 110 corresponds to the interior surface 108 such that the porous material 110 rests against the interior surface 108 substantially without forming any unoccupied spaces therebetween when no external forces pull the porous material 110 and the interior surface 108 apart.

However, the fluid collection assemblies disclosed herein may include at least one substantially unoccupied spaced between the interior surface of the fluid impermeable barrier and the porous material. The substantially unoccupied space is referred to herein as a fluid reservoir. In an example, the fluid reservoir may increase the volume of the bodily fluids that may be temporarily stored by the fluid collection assembly. For instance, the rate of bodily fluids introduced into the fluid collection assembly when an individual urinates may be greater than the rate at which the bodily fluids are removed from the fluid collection assembly. The substantially unoccupied space provides a location for the bodily fluids to pool while waiting to be removed from the fluid collection assembly. The substantially unoccupied space also minimizes oversaturation of the porous material which may cause the fluid collection assembly to leak or cause the bodily fluids to remain in contact with the individual thereby causing skin degradation and discomfort.

Figure 2A:
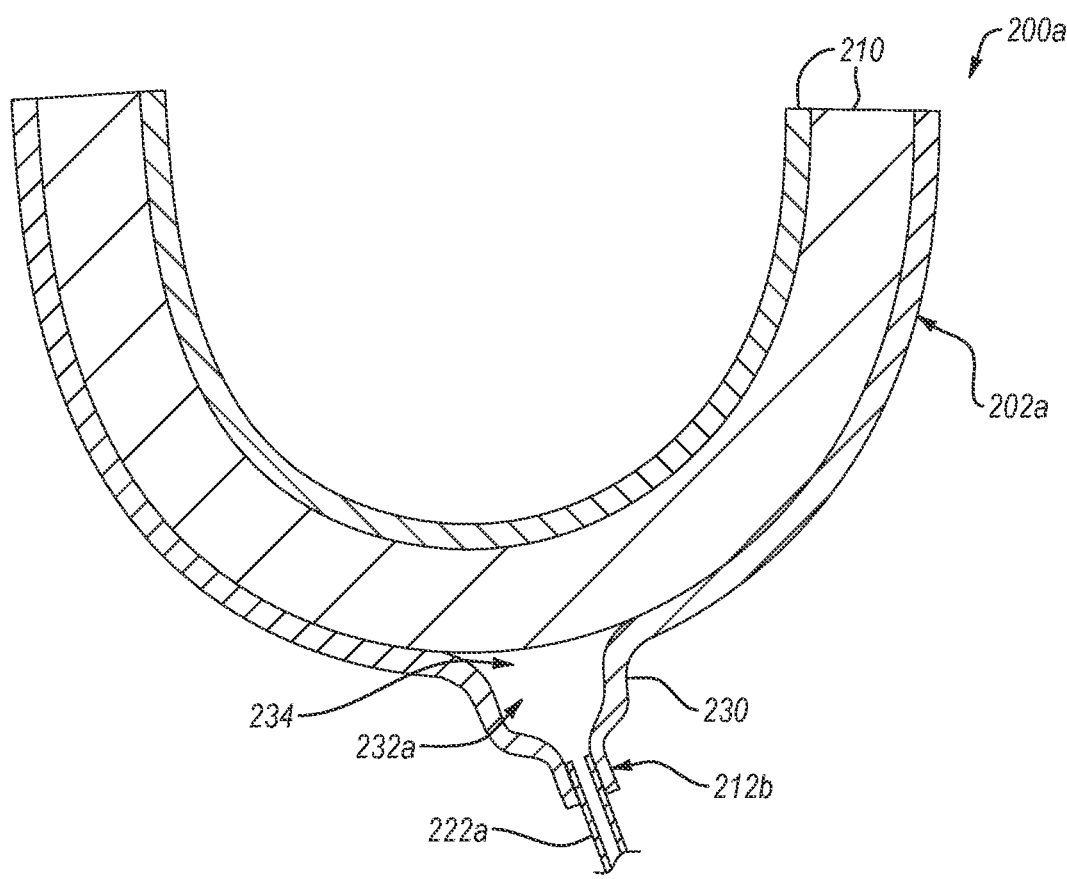
FIGS. 2A and 2B are cross-sectional views of fluid collection assemblies that include fluid reservoirs, according to different embodiments.
Figure 2B:
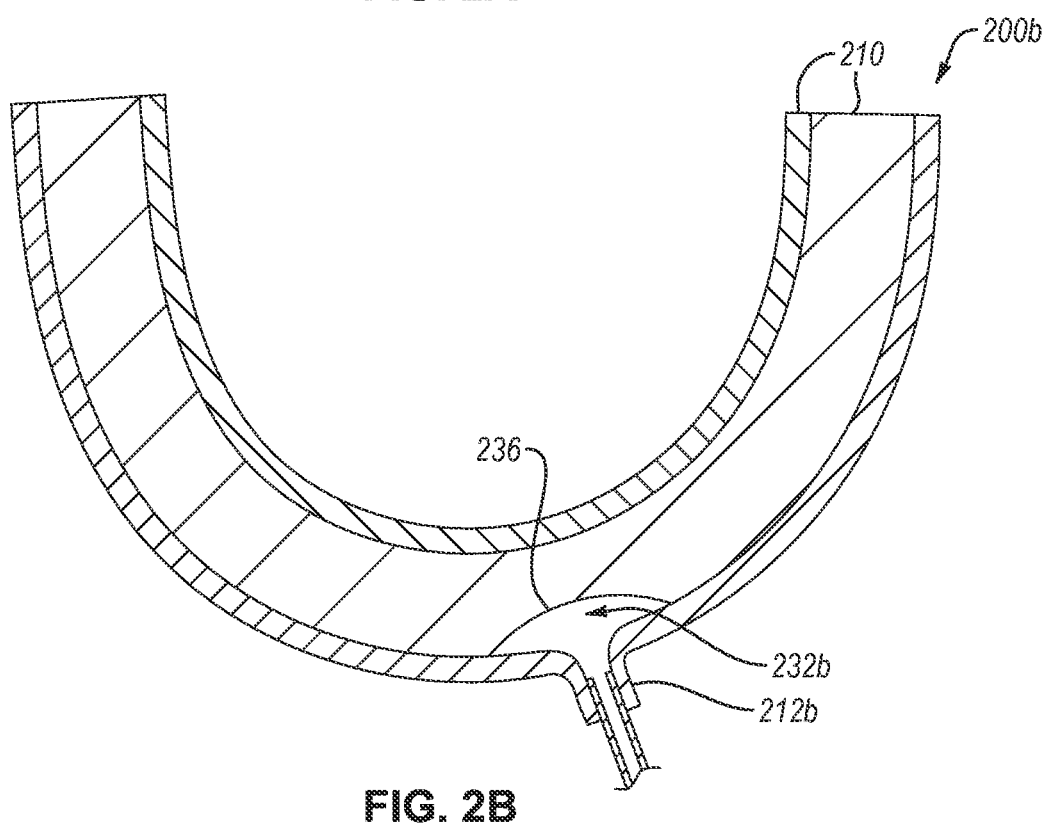

FIGS. 2A and 2B are cross-sectional views of fluid collection assemblies that include fluid reservoirs, according to different embodiments. Except as otherwise disclosed herein, the fluid collection assemblies of FIGS. 2A and 2B are substantially similar to any of the fluid collection assemblies disclosed herein. For example, the fluid collection assemblies of FIGS. 2A and 2B may include a fluid impermeable barrier defining a waist opening, two leg openings, and a fluid outlet. The fluid collection assemblies of FIGS. 2A and 2B may also include at least one porous material adjacent to a portion of an interior surface of the fluid collection assemblies. It is noted that the fluid collection assemblies illustrated in FIGS. 2A and 2B may be used in any of the fluid collection systems disclosed herein.

Referring to FIG. 2A, the fluid impermeable barrier 202a of the fluid collection assembly 200a includes a bulge 230 extending outwardly (e.g., away from the porous material 210a) from the rest of the fluid impermeable barrier 202a. The porous material 210a does not exhibit a shape that corresponds to the bulge 230 such that the bulge 230 defines a fluid reservoir 232a (e.g., substantially unoccupied space) that may temporarily store bodily fluids therein. For example, the bulge 230 may define an inlet 234. The porous material 210a may extend across the inlet 234 such that the porous material 210a substantially does not extend into the space defined by the bulge 230 or the porous material 210a may only extend partially into the space defined by the bulge 230. It is noted that the bulge 230 may make wearing the fluid collection assembly 200a less discrete since the bulge 230 is more likely to be noticeable through outerwear (e.g., the bulge 230 presses against pants or shorts worn by the individual) than if the fluid collection assembly 200a did not include the bulge 230.

In an embodiment, the fluid outlet 212b extends from, is formed by, or is otherwise in fluid communication with the bulge 230. As such, the fluid outlet 212b may remove bodily fluids temporarily stored in the bulge 230 thereby substantially preventing the bodily fluids from pooling in the fluid reservoir 232a. The bulge 230 may be located at or near the gravimetric low point of the fluid collection assembly 200a and the fluid outlet 212b may be located at or near the gravimetric low point of the bulge 230. For example, as previously discussed, bodily fluids received by the porous material 210a are preferentially drawn to the gravimetric low point of the fluid collection assembly 200. Thus, the bodily fluids may be preferentially drawn to and deposited in the bulge 230. Similarly, the bodily fluids deposited in the bulge 230 may be located at the gravimetric low point of the bulge 230. Locating the fluid outlet 212b at or near the gravimetric low point of the bulge 230 allows the fluid outlet 212b to remove bodily fluids from the fluid reservoir 232a. If the fluid outlet 212b is spaced from the gravimetric low point of the bulge 230 and the conduit 222a does not extend into the fluid reservoir 232a, the fluid outlet 212b may only remove bodily fluids from the bulge 230 when the quantity of the bodily fluids in the bulge 230 is sufficient to reach the fluid outlet 212b since the fluid reservoir 232a is substantially unoccupied.

Referring to FIG. 2B, the porous material 210b of the fluid collection assembly 200b defines a cutout 236 that does not conform to the interior surface 208 of the fluid impermeable barrier 202b. Thus, the cutout 236 forms a fluid reservoir 232b. However, the cutout 236 decreases the volume of the porous material 210b that may receive and temporarily retain the bodily fluids therein.

In an embodiment, the cutout 236 is adjacent to and/or surrounds the fluid outlet 212b. As such, the fluid outlet 212b may remove bodily fluids temporarily stored in the fluid reservoir 232b thereby substantially preventing the bodily fluids from pooling in the fluid reservoir 232b. The cutout 236 and the fluid outlet 212b may be located at or near the gravimetric low point of the fluid collection assembly 200b. For example, as previously discussed, bodily fluids received by the porous material 210b are preferentially drawn to the gravimetric low point of the fluid collection assembly 200b. Thus, the bodily fluids may be preferentially drawn to and deposited in the fluid reservoir 232b and allows the fluid outlet 212b to remove bodily fluids from the fluid reservoir 232b.

As previously discussed, the gravimetric low point of the fluid collection assemblies disclosed herein depend on the position of the individual. For example, the gravimetric low point of the fluid collection assembly may be at or near the intersection of the front and back portions of the fluid impermeable barrier when the individual is standing, on the back portion near the perineum and/or anus of the individual when the individual is sitting, on the back portion near the anus of the individual or between the anus and waist opening when the individual is laying down on the individual's back, or on the front portion when the individual is laying on the individual's stomach. Also, as previously discussed, the fluid collection assemblies disclosed herein allow the individual to move (e.g., switch from a sitting to a standing position). As such, moving the individual may cause the gravimetric low point of the fluid collection assembly to change. Fluid collection assemblies that only include a single fluid outlet may require the individual to assume a certain position when the individual discharges bodily fluids (e.g., urinates) or when the individual senses bodily fluids in the fluid collection assembly to ensure that fluid outlet is at or near the gravimetric low point. Alternatively, the fluid collection assemblies may include a plurality of fluid outlets to facilitate removal of the bodily fluids from the fluid collection assembly when the individual assumes a plurality of positions.

Figure 3A:
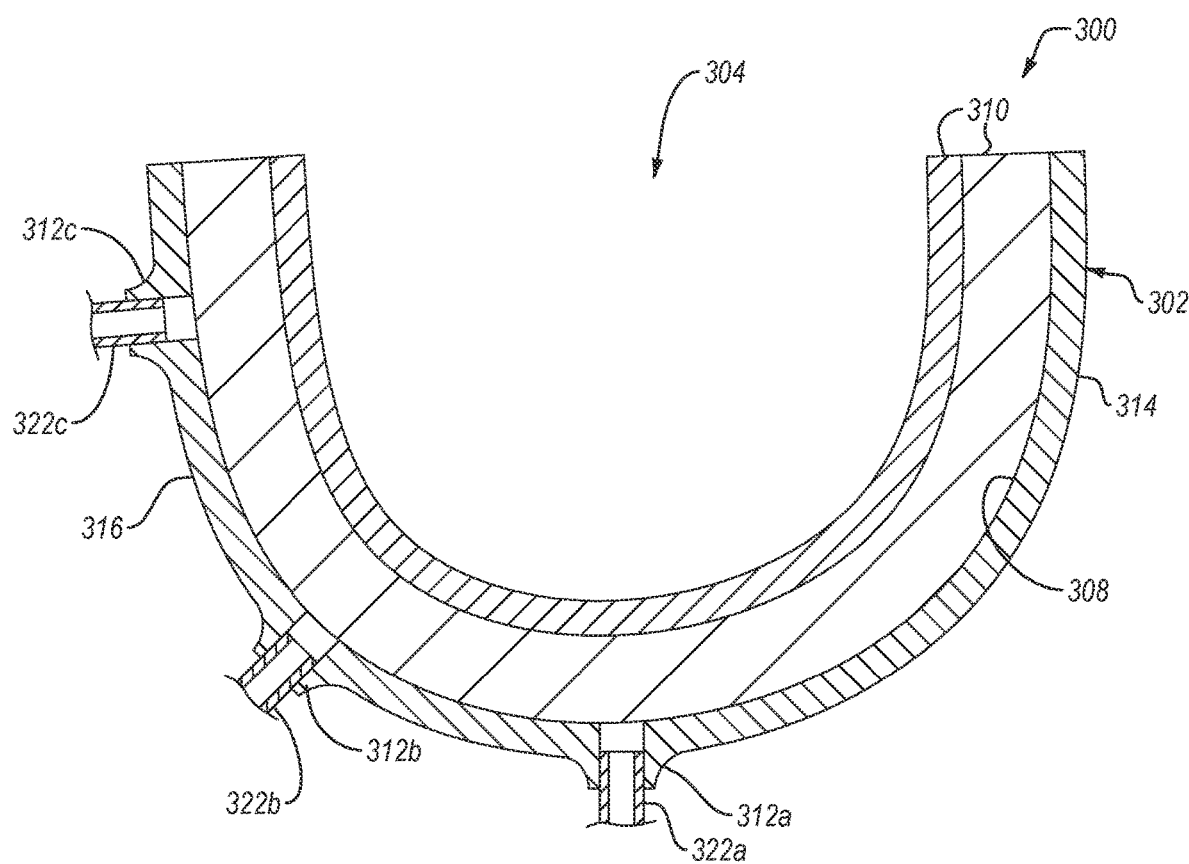
FIG. 3A is a cross-sectional schematic of a fluid collection assembly that includes a plurality of fluid outlets, according to an embodiment.

FIG. 3A is a cross-sectional schematic of a fluid collection assembly 300 that includes a plurality of fluid outlets, according to an embodiment. Except as otherwise disclosed herein, the fluid collection assembly 300 is the same or substantially similar to any of the fluid collection assemblies disclosed herein. For example, the fluid collection assembly 300 may include a fluid impermeable barrier 302 that defines a waist opening 304 and two leg openings (not shown). The fluid collection assembly 300 also includes at least one porous material 310 adjacent to at least a portion of an interior surface 308 of the fluid impermeable barrier 302. It is noted that the fluid collection assembly 300 may be used in any of the fluid collection systems disclosed herein.

The fluid impermeable barrier 302 defines a plurality of fluid outlets. For example, in the illustrated embodiment, the fluid impermeable barrier 302 defines a first fluid outlet 312a, a second fluid outlet 312b, and a third fluid outlet 312c. The first fluid outlet 312a may be configured to be at or near a gravimetric low point of the fluid collection assembly 300 when an individual using the fluid collection assembly 300 is standing. As such, the first fluid outlet 312a may be at or near an intersection of the front and back portions 314, 316 of the fluid impermeable barrier 302. The second fluid outlet 312b may be configured to be at or near a gravimetric low point of the fluid collection assembly 300 when an individual using the fluid collection assembly 300 is sitting. As such, the second fluid outlet 312b may be on the back portion 316 of the fluid impermeable barrier 302 at or near the perineum and/or anus of the individual. The third fluid outlet 312c may be configured to be at or near a gravimetric low point of the fluid collection assembly 300 when an individual using the fluid collection assembly 300 is lying on the individual's back. As such, the third fluid outlet 312c may be on the back portion 316 of the fluid impermeable barrier 302 near the anus of the individual or between the anus and waist opening 304. The fluid collection assembly 300 may include a first conduit 322a, a second conduit 322b, and a third conduit 322c coupled to the first fluid outlet 312a, the second fluid outlet 312b, and the third fluid outlet 312c. As such, the fluid collection assembly 300 may have substantially all the bodily fluid removed therefrom regardless if the individual using the fluid collection assembly 300 is standing, sitting, or lying on the individual's back.

It is noted that the fluid impermeable barrier 302 may define more (e.g., four, five, etc.) or less (e.g., two) than the three fluid outlets illustrated in FIG. 3A. Further, the fluid impermeable barrier 302 may define fluid outlets at locations other than the locations illustrated in FIG. 3A. In an example, the fluid impermeable barrier 302 may define fluid outlets that are located on the front portion 314 of the fluid impermeable barrier 302 closer to the waist opening 304 than the first fluid outlet 312a to facilitate the removal of bodily fluids when the individual is laying on the individual's stomach. In an example, the fluid impermeable barrier 302 may define fluid outlet that are located closer to one leg opening than another leg opening which may facilitate removal of bodily fluids when the individual is laying on the individual's side. In an example, the fluid impermeable barrier 302 may define fluid outlets that are located between the fluid outlets illustrated in FIG. 3A or otherwise disclosed herein. In such an example, the fluid outlets may facilitate the removal of bodily fluids when the individual is in an intermediate position, such as a slouching.

Figure 3B:
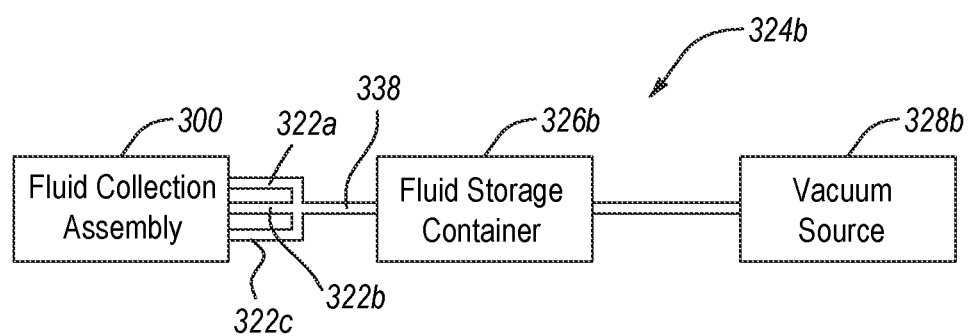
FIG. 3B is a block diagram of a fluid collection system that includes the fluid collection assembly illustrated in FIG. 3A, according to an embodiment.

FIG. 3B is a block diagram of a fluid collection system 324b that includes the fluid collection assembly 300 illustrated in FIG. 3A, according to an embodiment. Except as otherwise disclosed herein, the fluid collection system 324b may be the same or substantially similar to any of the systems disclosed herein. For example, the fluid collection system 324b may include a fluid storage container 326b and a vacuum source 326b that are in fluid communication with each other and with the fluid collection assembly 300 via one or more conduits.

As previously discussed, the fluid collection assembly 300 includes a first conduit 322a, a second conduit 322b, and a third conduit 322c. The first conduit 322a, the second conduit 322b, and the third conduit 322c may extend away from the fluid collection assembly 300 to a common conduit 338. The common conduit 338 may extend from the first conduit 322a, the second conduit 322b, and the third conduit 322c to the fluid storage container 326b, as shown, or to the vacuum source 328b. Any suction force applied to the common conduit 338 is also applied to the first conduit 322a, the second conduit 322b, and the third conduit 322c. It is noted that the fluid collection system 324b may include more or fewer conduits than the first conduit 322a, the second conduit 322b, and the third conduit 322c, depending on the number of fluid outlets formed in the fluid collection assembly 300.

Figure 3C:
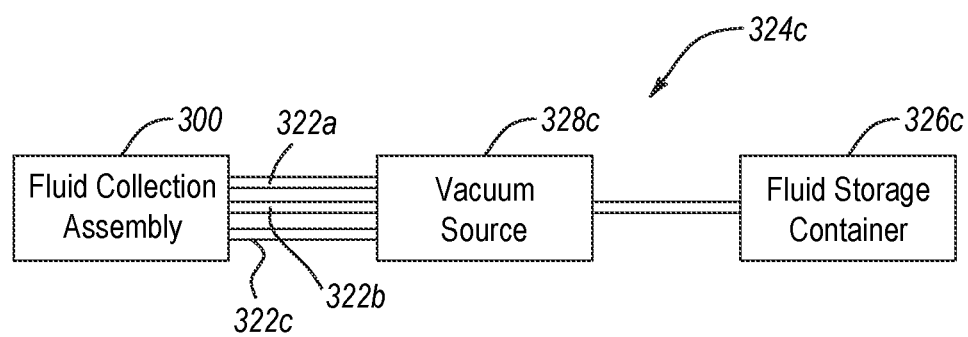
FIG. 3C is a block diagram of a fluid collection system that includes the fluid collection assembly illustrated in FIG. 3A, according to an embodiment.

FIG. 3C is a block diagram of a fluid collection system 324c that includes the fluid collection assembly 300 illustrated in FIG. 3A, according to an embodiment. Except as otherwise disclosed herein, the fluid collection system 324c may be the same or substantially similar to any of the systems disclosed herein. For example, the fluid collection system 324c may include a fluid storage container 326c and a vacuum source 328c that are in fluid communication with each other and with the fluid collection assembly 300 via one or more conduits.

As previously discussed, the fluid collection assembly 300 includes a first conduit 322a, a second conduit 322b, and a third conduit 322c. The first conduit 322a, the second conduit 322b, and the third conduit 322c may extend away from the fluid collection assembly 300. The first conduit 322a, the second conduit 322b, and the third conduit 322c may not intersection with each other but, instead may be in individually fluidly coupled to the vacuum source 328c (as shown) or to the fluid storage container 326c. As such, the vacuum source 328c may apply a suction force to one or more of the first conduit 322a, the second conduit 322b, and the third conduit 322c. It is noted that the fluid collection system 324c may include more or fewer conduits than the first conduit 322a, the second conduit 322b, and the third conduit 322c, depending on the number of fluid outlets formed in the fluid collection assembly 300.

With regards to the fluid collection system 324b illustrated in FIG. 3B or the fluid collection system 324c illustrated in FIG. 3C, a suction force provided to by the vacuum source of the system may be applied to all of the conduits coupled to the fluid outlets simultaneously (e.g., applied to the first conduit 322a, the second conduit 322b, and the third conduit 322c simultaneously) or may be applied selectively to only some of the conduits coupled to the fluid outlet (e.g., applied selectively to one or two of the first conduit 322a, the second conduit 322b, and the third conduit 322c). Applying the suction force to all of the conduits coupled to the fluid outlets simultaneously may allow for the removal of bodily fluids from the fluid collection assembly 300 using each of the fluid outlets. For example, applying the suction force to all of the conduits may allow for removal of the bodily fluids at or near the gravimetric low point of the fluid collection assembly and for the removal of the bodily fluids that are spaced from the gravimetric low point of the fluid collection assembly since, while the bodily fluids flow preferentially towards the gravimetric low point, some of the bodily fluids may flow away from the gravimetric low point due to the wicking. However, the suction force applied to the fluid outlet at the gravimetric low point may be less than if the suction force was only applied to the fluid outlet at the gravimetric low point thereby decreasing the rate at which the bodily fluids are removed from the fluid outlet at the gravimetric low point. Also, the suction force may preferentially remove air from the fluid collection assembly than liquids. Thus, applying the suction force to each of the fluid outlets may reduce the rate at which bodily fluids are removed from the fluid collection assembly when one of the fluid outlets is exposed to air.

Alternatively, the fluid collection systems 324b and/or 324c may be configured to apply the suction force selectively to some of the conduits coupled to the fluid outlets of the fluid collection assembly. Selectively applying the suction force may mitigate issues caused by the suction force preferentially pulling air instead of bodily fluids and increase the suction force applied to the fluid outlet that is exposed to bodily fluids. In an example, the first conduit 322a, the second conduit 322b, and the third conduit 322c of the fluid collection system 324b illustrated in FIG. 3B may include valves that selectively open (e.g., allow a flow of the suction force through the conduit) or close (e.g., restriction a flow the suction force through the conduit). In other words, the valves may be used to apply the suction force to selected one(s) of the conduits coupled to the fluid outlets of the fluid collection assembly. In an example, the vacuum source 328c of the fluid collection system 324c illustrated in FIG. 3C may be configured to selectively apply the suction force to selected one(s) of the conduits coupled to the fluid outlets of the fluid collection assembly.

Figure 4:
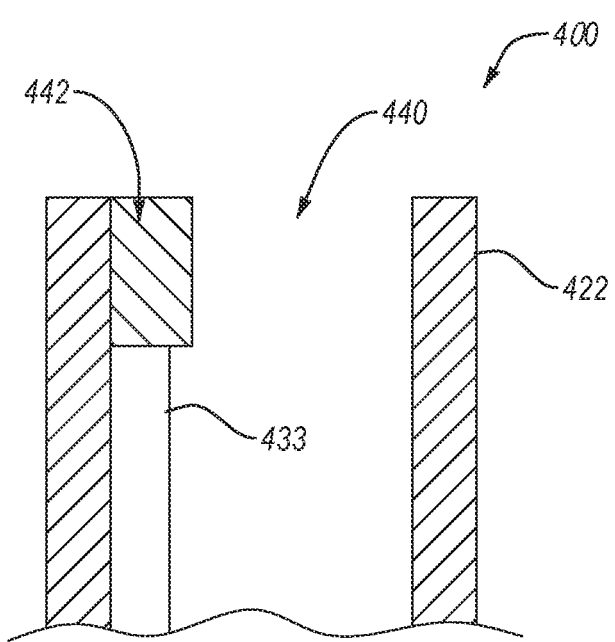
FIG. 4 is a cross-sectional schematic of a portion of a fluid collection assembly, according to an embodiment.

FIG. 4 is a cross-sectional schematic of a portion of a fluid collection assembly 400, according to an embodiment. Except as otherwise disclosed herein, the fluid collection assembly 400 may be the same or substantially similar to any of the fluid collection assemblies disclosed herein. For example, the fluid collection assembly 400 includes a conduit 422. The conduit 422 includes an inlet 440 that is positioned within or proximate to (e.g., inside the fluid reservoir) to a fluid outlet (not shown). The inlet 440 allows the conduit 422 to receive bodily fluids.

The fluid collection assembly 400 includes a sensor 442 that is configured to detect a presence of moisture (e.g., moisture caused by the presence of bodily fluids). The sensor 442 may be configured to detect the presence of moisture directly or indirectly (e.g., detect the absence of air). The sensor 442 may include any sensor that may detect the presence of moisture, such as one or more of an electrochemical gas sensor, a humistor, a hygrometer, a flow meter, a pH sensor, or two or more electrodes.

In an embodiment, the sensor 442 is disposed in the conduit 422. In such an embodiment, the sensor 442 may determine whether the conduit 422 is removing air or bodily fluids from the rest of the fluid collection assembly 400. In an embodiment, the sensor 442 is disposed outside of the conduit 422, such as proximate to the conduit 422 and at least one of in a fluid reservoir, adjacent to the fluid impermeable barrier, or within the porous material. In such an embodiment, the sensor 442 may detect the presence of the bodily fluids even when the bodily fluids are not flowing through the conduit 422 (e.g., when a suction force is not applied to the conduit 422). In an embodiment, the sensor 442 is disposed at the inlet 440 of the conduit 422 which allows the sensor 442 to detect when the bodily fluids are flowing through the conduit 422 and the presence of the bodily fluids even when the bodily fluids are not flowing through the conduit 422.

The sensor 442 may be communicably coupled to one or more components of a fluid collection system (not shown) via a wired connection 443 (as shown) or a wireless connection. For example, a fluid collection system that include the fluid collection assembly 400 may include a controller having control electrical circuitry (not shown). The controller may include non-transitory memory storing one or more operational instructions and at least one processor configured to execute the operational instructions. The controller may be communicably coupled to the sensor 442 and one or more components of the fluid collection system (e.g., the one or more valves or the vacuum source). The controller may receive one or more signals from the sensor 442. The signals may indicate whether the sensor 442 detected or did not detect bodily fluids. The controller may control the operation of the valves and/or the vacuum source response to the signals from the sensor 442. For example, responsive to instructions from the controller, the valves or vacuum source may be configured to selectively apply a suction force to the conduit 422 depending on whether the sensor 442 detected or did not detect the bodily fluids. In an embodiment, the fluid collection assembly 400 may include a plurality of conduits, similar to the embodiments discussed with regards to FIGS. 3A-3C. In such an embodiment, the controller may direct the valves and/or vacuum source to apply the suction force only to the conduit(s) associated with sensor(s) 442 that detected bodily fluids to increase the suction force applied to such conduits and to minimize air that is pulled through the conduit(s). In an embodiment, the control electrical circuitry may direct the vacuum source to only apply a suction force to the conduit 422 when the sensor 442 detects the presence of the bodily fluids. Applying the suction force only when the sensor 442 detects the presence of the bodily fluids may reduce the time periods during which the vacuum source generates noise thereby allowing the fluid collection assembly 400 to be used more discretely.

It is noted that the suction force applied to the conduit 422 may be controlled in other ways, including with or without the sensor 442. In an example, the valves may include actuators that may be manipulated by the individual. Manipulating the valves may switch the valves between an open and closed state. In an example, the vacuum source may include one or more actuators (e.g., buttons) and manipulating the actuator may cause the vacuum source to at least one of selectively apply the suction source to one or more of the conduits or turn on and off the vacuum source.

As previously discussed, the fluid collection systems disclosed herein may be used with any suitable vacuum source. In an embodiment, the fluid collection systems disclosed herein include a vacuum source that include an in-the-wall vacuum source (e.g., an access port, such as inlet, of the in-the-wall vacuum source in provided at a wall) or a plugged-in vacuum source. In such an embodiment, the distance that an individual wearing a fluid collection assembly may move is limited by the length of the conduit that connects the individual to the in-the-wall vacuum source or the plugged-in vacuum source. As such, the mobility of the individual is limited even though the fluid collection assembly worn by the individual allows for significant movement.

Figure 5:
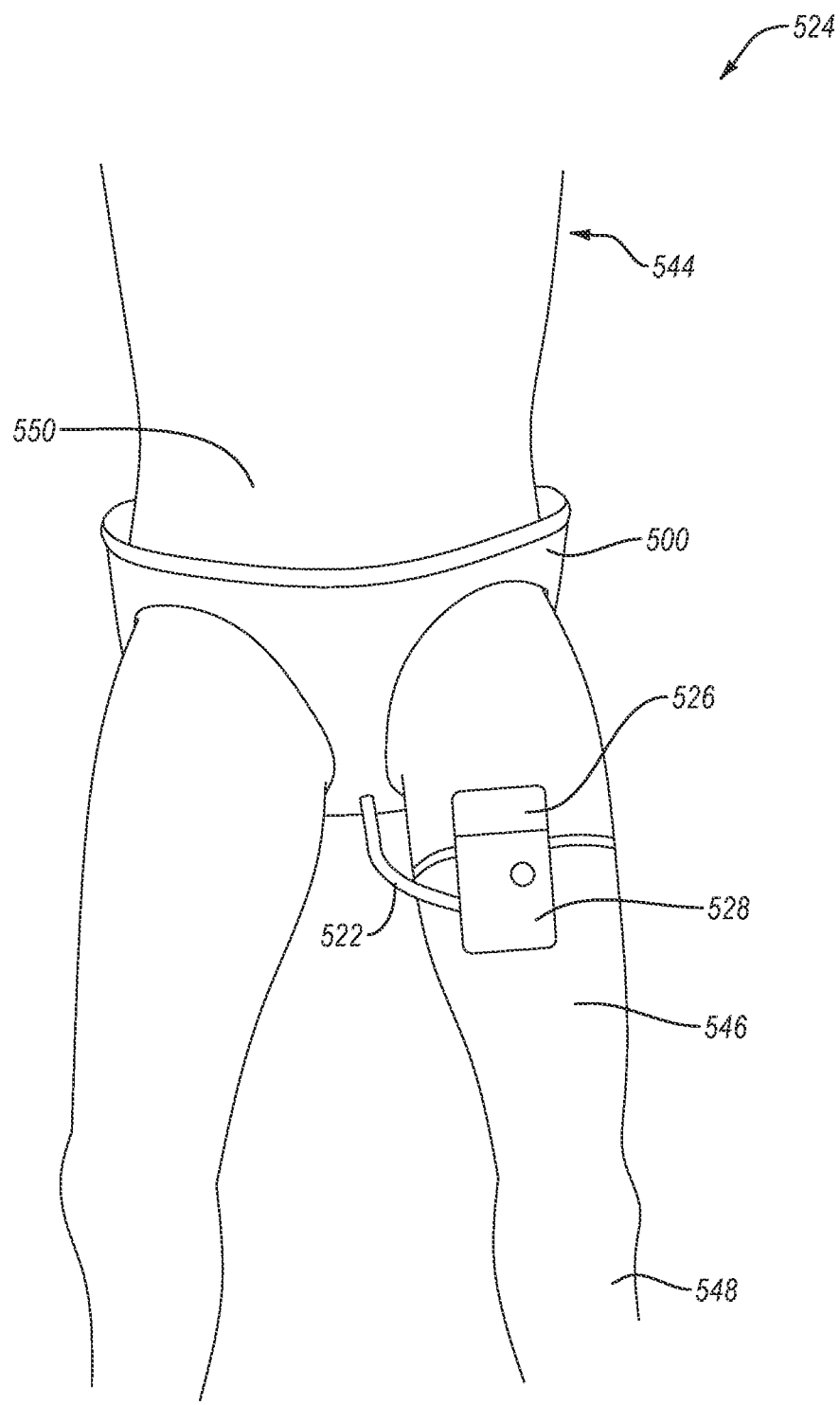
FIG. 5 is an isometric view of a fluid collection system that includes a portable vacuum source on an individual, according to an embodiment.

In an embodiment, the fluid collection systems disclosed herein may include a portable vacuum source which allows the individual wearing any of the fluid collection assemblies disclosed herein significant movement. FIG. 5 is an isometric view of a fluid collection system 524 that includes a portable vacuum source 528 on an individual 544, according to an embodiment. Except as otherwise disclosed herein, the fluid collection system 524 may be the same or substantially similar to any of the fluid collection systems disclosed herein. For example, the fluid collection system 524 may include a fluid collection assembly 500. The fluid collection assembly 500 may include any of the fluid collection assemblies disclosed herein. The fluid collection system 524 also includes a fluid storage container 526 and the vacuum source 528. The fluid storage container 526 and the vacuum source 528 may be in fluid communication with the fluid collection assembly 500 via at least one conduit 522.

The fluid storage container 526 and the vacuum source 528 are configured to be worn by the individual 544. For example, in the illustrated embodiment, the fluid storage container 526 and the vacuum source 528 are configured to be attached to the thigh 546 of the individual 544. In such an example, the fluid storage container 526 and the vacuum source 528 exhibit a size and shape that allows the fluid storage container 526 and the vacuum source 528 to be positioned on the thigh 546 of the individual 544. For instance, the fluid storage container 526 and the vacuum source 528 collectively may exhibit a length measured along a longitudinal axis of the thigh 546 that is less than a 25 cm (e.g., less than 20 cm, less than 15 cm, or less than 10 cm), a width that is less than 20 cm (e.g., less than 15 cm, less than 10 cm, less than 7.5 cm, or less than 5 cm), and a thickness that is less than 7.5 cm (e.g., less than 5 cm, less than 4 cm, less than 3 cm, or less than 2 cm). Such sizes may allow the fluid storage container 526 and the vacuum source 528 to be worn discretely on the thigh 546 of the individual 544. Further, the fluid storage container 526 and the vacuum source 528 may include a concave surface that is configured to mate with the thigh 546 of the individual 544 since such a concave surface may make wearing the fluid storage container 526 and the vacuum source 528 more comfortable. The fluid storage container 526 and the vacuum source 528 may be attached to the thigh 546 using any suitable attachment mechanism, such as with a strap or an adhesive.

It is noted that the fluid storage container 526 and the vacuum source 528 may be configured to be worn on a different area of the individual 544. In an example, the fluid storage container 526 and the vacuum source 528 may be configured to be worn on the calf 548 or abdominal region 550 of the individual. In such an example, the fluid storage container 526 and the vacuum source 528 may exhibit any of the size or shapes discussed above. In an example, the fluid storage container 526 and the vacuum source 528 may be configured to be disposed in a pocket or attached to a belt.

Figure 6:
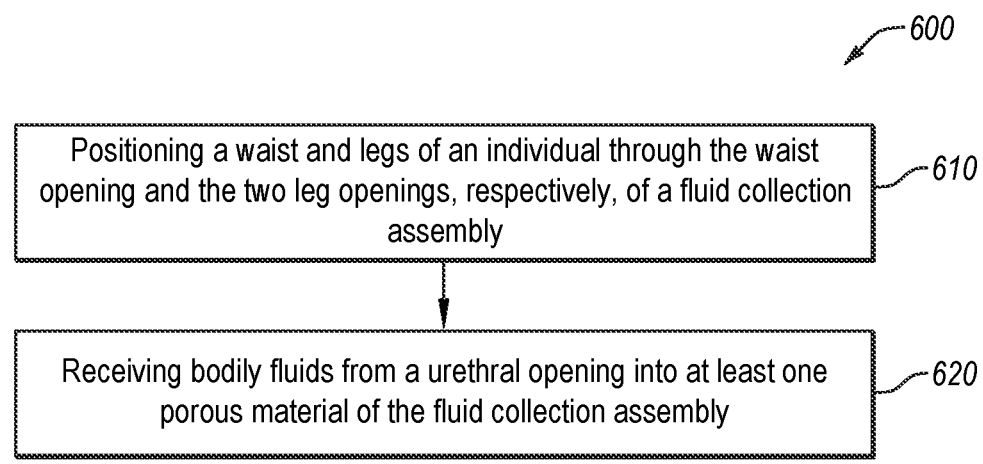
FIG. 6 is a flow diagram of a method to collect fluid, according to an embodiment.

FIG. 6 is a flow diagram of a method 600 to collect fluid, according to an embodiment. The method 600 of collecting fluid may utilize use any of the fluid collection assemblies and/or fluid collection systems disclosed herein. The method 600 may include act 610, which recites "positioning a waist and legs of an individual through the waist opening and the two leg openings, respectively, of a fluid collection assembly." Act 610 may be followed by act 620, which recites "receiving bodily fluids from a urethral opening into at least one porous material of the fluid collection assembly."

Acts 610, 620 of the method 600 are for illustrative purposes. For example, the act 610, 620 of the method 600 may be performed in different orders, split into multiple acts, modified, supplemented, or combined. In an example, one or more of the acts 610, 620 of the method 600 may be omitted from the method 600. Any of the acts 610 or 620 may include using any of the fluid collection assemblies or systems disclosed herein.

Act 610 recites "positioning a waist and legs of an individual through the waist opening and the two leg openings, respectively, of a fluid collection assembly." The act 610 of may include utilizing any of the fluid collection assemblies or systems disclosed herein. In some examples, act 610 may include positioning the fluid collection assembly such that the porous material of the fluid collection assembly abuts or is positioned proximate to the female or male urethral opening.

Act 620 recites "receiving bodily fluids from a urethral opening into at least one porous material of the fluid collection assembly." In some examples, receiving bodily fluids from a urethral opening (e.g., female or male urethral opening) into porous material of the fluid collection assembly may include wicking the bodily fluids using the at least one porous material, such as via a fluid permeable membrane and a fluid permeable support. Receiving bodily fluids from the urethral opening may include flowing the bodily fluids towards a fluid outlet For instance, receiving fluid from the urethral opening may include flowing the bodily fluids to a substantially unoccupied portion (e.g., a fluid reservoir), to a gravimetrically low point of the fluid collection assembly, etc., such as via gravity, wicking, or suction force.

The method 600 may include applying suction with a vacuum source effective to suction the bodily fluids from the fluid collection assembly via a conduit disposed therein and fluidly coupled to the vacuum source may include using any of the vacuum sources disclosed herein. Applying suction with a vacuum source may include activating the vacuum source (e.g., suction device) in fluid communication with the conduit in the fluid collection assembly. In some examples, activating the vacuum source in fluid communication with the conduit in the fluid collection assembly may include supplying power to the vacuum source by one or more of flipping an on/off switch, pressing a button, plugging the vacuum source into a power outlet, putting batteries into the vacuum source, etc. In some examples, the vacuum source may include a hand operated vacuum pump and applying suction with a vacuum source may include manually operating the hand operated vacuum pump effective to suction the bodily fluids from the fluid collection assembly via the conduit disposed therein that is fluidly coupled to the vacuum source.

In some examples, applying suction with a vacuum source effective to suction the bodily fluids via a conduit disposed therein and fluidly coupled to the vacuum source may be effective to remove at least some bodily fluids (e.g., urine) from the fluid collection assembly. In some examples, applying suction with a vacuum source effective to suction the bodily fluids from the fluid collection assembly via a conduit disposed therein and fluidly coupled to the vacuum source may be effective to transfer at least some of the bodily fluids to a fluid storage container (e.g., a bottle or bag), such as from one or more of a reservoir, fluid permeable support, or fluid permeable membrane.

In some examples, applying suction with a vacuum source effective to suction the bodily fluids via a conduit disposed therein and fluidly coupled to the vacuum source may include detecting moisture in the porous material (e.g., via one or more moisture sensors) and responsive thereto, activating the vacuum source to provide suction in the fluid collection assembly. The control of the vacuum source responsive to the signals indicating that moisture or a level thereof is present in the fluid collection assembly may be automatic, such as via a controller (e.g., computer programmed to perform the operation), or may merely provide an indication that a level of moisture is present that may necessitate removal of fluid from the fluid collection assembly. In the latter case, a user may receive the indication (e.g., from the controller) and activate the vacuum pump manually.

In an example, the method 600 may include collecting the bodily fluids that are removed from the fluid collection assembly, such as into a fluid storage container that is spaced from the fluid collection assembly and fluidly coupled to the conduit. The fluid storage container may include any of the fluid storage containers disclosed herein.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean ±10%, ±5%, or +2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

I claim:

1. A fluid collection assembly, comprising:
   a fluid impermeable barrier at least partially defining:
      a waist opening;
      two leg openings; and
      at least one fluid outlet spaced from exterior edges of the fluid impermeable barrier and edges of the fluid impermeable barrier that at least partially define the two leg openings; and
   at least one porous material generally conforming to at least a portion of the fluid impermeable barrier, the at least one porous material extending from or near a portion of the waist opening to or near an opposing portion of the waist opening, the at least one porous material including:
      a fluid permeable membrane positioned to contact an individual, the fluid permeable membrane configured to receive and wick bodily fluids away from the individual; and
      a fluid permeable support configured to have the bodily fluids flow therein, the fluid permeable support abuts substantially all of an interior surface of the fluid impermeable barrier that is not immediately adjacent to the at least one fluid outlet.

2. The fluid collection assembly of claim 1, wherein the at least one fluid outlet is configured to be located at or near a gravimetric low point of the fluid impermeable barrier when an individual wearing the fluid collection assembly is at least one of standing, sitting, or lying down.

3. The fluid collection assembly of claim 2, wherein the at least one fluid outlet includes a fluid outlet at or near a portion of the fluid impermeable barrier adjacent to a perineum or genitalia of the individual.

4. The fluid collection assembly of claim 2, wherein the at least one fluid outlet includes a fluid outlet at or near a portion of the fluid impermeable barrier adjacent to at least one of a perineum or an anus of the individual.

5. The fluid collection assembly of claim 2, wherein the at least one fluid outlet includes a fluid outlet that is between the waist opening and an anus of the individual.

6. The fluid collection assembly of claim 1, further comprising at least one conduit in fluid communication with the at least one fluid outlet.

7. The fluid collection assembly of claim 1, further comprising at least one fluid reservoir proximate to the at least one fluid outlet and between the fluid impermeable barrier and at least one porous material, wherein the at least one fluid reservoir is empty space.

8. The fluid collection assembly of claim 7, wherein the fluid impermeable barrier includes a bulge that directly and partially defines the at least one fluid reservoir.

9. The fluid collection assembly of claim 7, wherein the at least one porous material includes at least one concave surface directly defining a cutout, the at least one fluid reservoir is partially defined by the cutout.

10. The fluid collection assembly of claim 1, wherein the fluid collection assembly does not include an adsorbent or absorbent material.

11. The fluid collection assembly of claim 1, wherein the fluid collection assembly is configured for single use.

12. The fluid collection assembly of claim 1, wherein the at least one fluid outlet includes a plurality of fluid outlets and each of the plurality of fluid outlets are spaced from the exterior edges of the fluid impermeable barrier and the edges of the fluid impermeable barrier that at least partially define the two leg openings.

13. The fluid collection assembly of claim 12, further comprising a plurality of conduits attached to each of the plurality of fluid outlets, the plurality of tubes distinct and separate from the plurality of fluid outlets.

14. The fluid collection assembly of claim 1, wherein the at least one porous material includes at least one of fabric, felt, gauze, a plurality of fibers, or an open cell foam.

15. The fluid collection assembly of claim 1, wherein the fluid permeable support includes at least one of a porous polymer, an open cell foam, cotton, wool, silk, fabric, felt, or gauze.

16. The fluid collection assembly of claim 9, wherein the fluid permeable support defines all of the at least one concave surface.

17. The fluid collection assembly of claim 1, further comprising at least one fluid reservoir proximate to the at least one fluid outlet, the at least one fluid reservoir completely defined by the fluid impermeable barrier, the fluid permeable support, and the conduit, wherein the at least one fluid reservoir is empty space.

18. The fluid collection assembly of claim 1, further comprising at least one fluid reservoir proximate to the at least one fluid outlet, the fluid permeable support positioned between the fluid permeable membrane and the at least one fluid reservoir spaced and spacing the fluid permeable membrane from the at least one fluid reservoir.

19. The fluid collection assembly of claim 1, wherein the fluid permeable support abuts substantially all of an interior surface of the fluid impermeable barrier.

20. The fluid collection assembly of claim 1, wherein the fluid permeable support extends continuously from or near a back portion of the waist opening to or near a front portion of the wait opening and from or near one of the two leg openings to or near the other one of the two leg openings, the back portion configured to be positioned adjacent to a back side of an individual and the front portion configured to be positioned adjacent to a front side of the individual.

21. The fluid collection assembly of claim 1, wherein the fluid collection assembly is washable.

22. A fluid collection assembly, comprising:
- a fluid impermeable barrier at least partially defining:
  - a waist opening;
  - two leg openings; and
  - at least one fluid outlet spaced from exterior edges of the fluid impermeable barrier and edges of the fluid impermeable barrier that at least partially define the two leg openings;
- at least one porous material generally conforming to at least a portion of the fluid impermeable barrier, the at least one porous material extending from or near a portion of the waist opening to or near an opposing portion of the waist opening, the at least one porous material including:
  - a fluid permeable membrane positioned to contact an individual, the fluid permeable membrane configured to receive and wick bodily fluids away from the individual; and
  - a fluid permeable support configured to have the bodily fluids flow therein; and
- at least one fluid reservoir proximate to the at least one fluid outlet, the at least one fluid reservoir completely defined by the fluid impermeable barrier, the fluid permeable support, and the conduit, wherein the at least one fluid reservoir is empty space.

* * * * *